US009217011B2

(12) United States Patent
Desmet et al.

(10) Patent No.: US 9,217,011 B2
(45) Date of Patent: Dec. 22, 2015

(54) NON-NATURAL PROTEINACEOUS SCAFFOLD MADE OF THREE NON-COVALENTLY ASSOCIATED PEPTIDES

(75) Inventors: Johan Desmet, Kortrijk (BE); Ignace Lasters, Antwerp (BE)

(73) Assignee: Complix NV, Ghent (BE)

( * ) Notice: Subject to any disclaimer, the term of this patent is extended or adjusted under 35 U.S.C. 154(b) by 0 days.

(21) Appl. No.: 12/676,783

(22) PCT Filed: Sep. 8, 2008

(86) PCT No.: PCT/EP2008/061886

§ 371 (c)(1), (2), (4) Date: Mar. 23, 2010

(87) PCT Pub. No.: WO2009/030780

PCT Pub. Date: Mar. 12, 2009

(65) Prior Publication Data

US 2010/0305304 A1 Dec. 2, 2010

Related U.S. Application Data

(60) Provisional application No. 60/970,607, filed on Sep. 7, 2007.

(51) Int. Cl.
*C07K 14/00* (2006.01)
*C07K 1/00* (2006.01)
*C07K 7/08* (2006.01)

(52) U.S. Cl.
CPC ... *C07K 1/00* (2013.01); *C07K 7/08* (2013.01); *C07K 14/001* (2013.01); *C07K 2318/20* (2013.01)

(58) Field of Classification Search
None
See application file for complete search history.

(56) References Cited

U.S. PATENT DOCUMENTS

| | | | | |
|---|---|---|---|---|
| 5,824,483 | A | 10/1998 | Houston, Jr. et al. | |
| 6,303,317 | B1 | 10/2001 | Alber et al. | |
| 6,828,106 | B2 * | 12/2004 | Colyer et al. | 435/7.1 |
| 6,872,806 | B1 | 3/2005 | Kondejewski et al. | |
| 7,053,179 | B2 | 5/2006 | Root et al. | |
| 7,262,272 | B2 | 8/2007 | Kondejewski et al. | |
| 2003/0021795 | A1 | 1/2003 | Houston et al. | |
| 2006/0014139 | A1 | 1/2006 | Root et al. | |
| 2008/0027006 | A1 | 1/2008 | Tripet et al. | |
| 2011/0294983 | A1 | 12/2011 | Desmet et al. | |
| 2012/0177676 | A1 | 7/2012 | Desmet et al. | |

FOREIGN PATENT DOCUMENTS

| | | | |
|---|---|---|---|
| WO | WO 97/00267 | | 1/1997 |
| WO | WO 98/56906 | | 12/1998 |
| WO | WO 99/16883 | | 4/1999 |
| WO | WO 2005/018666 | A1 | 3/2005 |
| WO | WO 2005/077103 | A2 | 8/2005 |
| WO | WO 2005/118886 | A2 | 12/2005 |

OTHER PUBLICATIONS

Arndt et al., "Helix-stabilized Fv (hsFv) Antibody Fragments: Substituting the Constant Domains of a Fab Fragment for a Heterodimeric Coiled-coil Domain," *J. Mot. Biol.* 312:221-228, 2001.
Baker et al., "Structural Basis for Paramyxovirus-Mediated Membrane Fusion," *Mol. Cell* 3:309-319, 1999.
Binz et al., "Engineering novel binding proteins from nonimmunoglobulin domains," *Nat. Biotechnol.* 23:1257-1268, 2005.
Bleicher et al., "Hit and Lead Generation: Beyond High-Throughput Screening," *Nat. Rev. Drug Disco.* 2:369-378, 2003.
Bosch et al., "Severe acute respiratory syndrome coronavirus (SARS-CoV) infection inhibition using spike protein heptad repeat-derived peptides," *Proc. Natl. Acad. Sci.* USA 101:8455-8460, 2004.
Burkhard et al., "Coiled coils: a highly versatile protein folding motif," *Trends Cell Biol.* 11:82-88, 2001.
Chan et al., "Core Structure of gp41 from the HIV Envelope Glycoprotein," *Cell* 89:263-273, 1997.
Conway and Parry, "Three-stranded α-fibrous proteins: the heptad repeat and its implications for structure," *Int. J. Biol. Macromol.* 13:14-16, 1991.
Database Geneseq, "SARS Coronavirus S Protein Residues 1151-1185 HR-C4 Analog 1," Accession No. AEC05353 (Nov. 3, 2005).
Dragan and Privalov, "Unfolding of a Leucine zipper is not a Simple Two-state Transition," *J. Mol. Biol.* 321:891-908, 2002.
Dragan et al., "Kinetics and Thermodynamics of the Unfolding and Refolding of the Three-Stranded α-Helical Coiled Coil, Lpp-56," *Biochemistry* 43:14891-14900, 2004.
Dunker et al., "On the Importance of Being Disordered," *PDB Newsletter* 81:3-5, 1997.
Dwyer et al., "The Hydrophobic Pocket Contributes to the Structural Stability of the N-Terminal Coiled Coil of HIV gp41 but Is Not Required for Six-Helix Bundle Formation," *Biochemistry* 42:4945-4953, 2003.
Eaton et al., "Let's get specific: the relationship between specificity and affinity," *Chem. Biol.* 2:633-638, 1995.
Eckert et al., "Crystal Structure of GCN4-pI$_Q$I, a Trimeric Coiled Coil with Buried Polar Residues," *J. Mol. Biol.* 284:859-865, 1998.

(Continued)

*Primary Examiner* — Thomas S Heard
(74) *Attorney, Agent, or Firm* — Clark & Elbing LLP

(57) ABSTRACT

The present invention is related to a non-natural, thermodynamically stable, proteinaceous scaffold consisting of three non-covalently associated peptides, wherein each peptide sequence comprises less than fifty amino acid residues and wherein at least 50% of the said residues are substitutable amino acids into at least ten different amino acid residue types. The present invention is further related to a non-natural, triple-stranded, parallel alpha-helical coiled coil scaffold wherein each of the three constituting peptide sequences comprise between 2 and 7 consecutive heptad repeats of the formula cxxcxxx (SEQ ID NO: 10), wherein at least 70% of the core c-residues are isoleucines, wherein all non-core x-residues are alanines, and wherein the constituting peptide sequences remain associated under physical conditions that are significantly different from physiological conditions.

14 Claims, 6 Drawing Sheets

(56) References Cited

OTHER PUBLICATIONS

Figure 1:
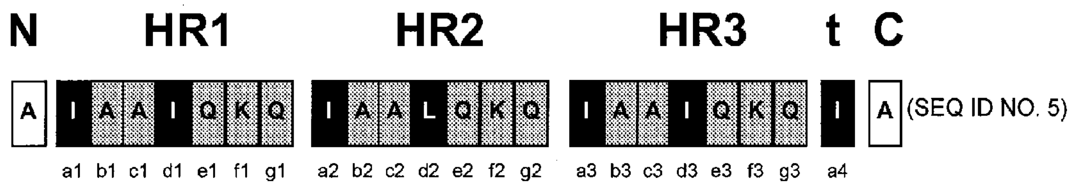

Eckert and Kim, "Design of potent Inhibitors of HIV-1 entry from the gp41 N-peptide region," *Proc. Natl. Acad. Sci.* USA 98:11187-11192, 2001.
Efimov et al., "Fibritin Encoded by Bacteriophage T4 Gene wac has a Parallel Triple-stranded α-Helical Coiled-coil Structure," *J. Mol. Biol*. 242:470-486, 1994.
Engels and Venkatarangan, "Smart screening: Approaches to efficient HTS," *Curr. Opin. Discov. Devel*. 4:275-283, 2001.
Hansen et al., "Intrinsic Protein Disorder, Amino Acid Composition, and Histone Terminal Domains," *J. Biol. Chem.* 281:1853-1856, 2006.
Harbury et al., "A Switch Between Two-, Three-, and Four-Stranded Coiled Coils in GCN4 Leucine Zipper Mutants," *Science* 262:1401-1407, 1993.
Harbury et al., "Crystal structure of an isoleucine-zipper trimer," *Nature* 371: 80-83, 1994.
Harris et al., "Four Helix Bundle Diversity in Globular Proteins," *J. Mol. Biol*. 236:1356-1368, 1994.
Holton and Alber, "Automated protein crystal structure determination using ELVES," *Proc. Natl. Acad. Sci.* USA 101:1537-1542, 2004.
Hosse et al., "A new generation of protein display scaffolds for molecular recognition," *Protein Sci*. 15:14-27, 2006.
Kiyokawa et al., "Engineering of the Hydrophobic Core of an α-Helical Coiled Coil," *Biopolymers* 55:407-414, 2000.
Koshiba and Chan, "The Prefusogenic Intermediate of HIV-1 gp41 Contains Exposed C-peptide Regions," *J. Biol. Chem.* 278:7573-7579, 2003.
Lovejoy et al., "Crystal Structure of a Synthetic Triple-Stranded α-Helical Bundle," *Science* 259:1288-1293, 1993.
Ludwig et al., "The 3D structure of the fusion primed Sendai F-protein determined by electron cryomicroscopy," *EMBO J.* 22:3761-3771, 2003.
Lumb and Kim, "Measurement of Interhelical Electrostatic Interactions in the GCN4 Leucine Zipper," *Science* 268: 436-439, 1995.
Lupas, "Coiled coils: new structures and new functions," *Trends Biochem. Sci*. 21:375-382, 1996.
Lupas et al., "Predicting Coiled Coils from Protein Sequences," *Science* 252:1162-1164, 1991.
Mason and Arndt, "Coiled Coil Domains: Stability, Specificity, and Biological Implications," *Chembiochem*. 5:170-176, 2004.
Moitra et al., "Life without white fat: a transgenic mouse," *Genes Dev*. 12:3168-3181, 1998.
Müller et al., "Protein Fusions to Coiled-Coil Domains," *Methods Enzymol* 328:261-282, 2000.
Naik et al., "The thermostability of an α-helical coiled-coil protein and its potential use in sensor applications," *Biosens. Bioelectron* 16:1051-1057, 2001.
Nautiyal and Alber, "Crystal structure of a designed, thermostable, heterotrimeric coiled coil," *Protein Sci*. 8:84-90, 1999.
Phelan et al., "Salt Bridges Destabilize a Leucine Zipper Designed for Maximized Ion Pairing Between Helices," *Biochemistry* 41:2998-3008, 2002.
Ryadnov et al., "'Belts and Braces': A Peptide-Based Linker System of de Novo Design," *J. Am. Chem. Soc*. 125:9388-9394, 2003.
Skerra, "Engineered protein scaffolds for molecular recognition," *J. Mol. Recognit*. 13:167-187, 2000.
Suzuki et al., "An isoleucine zipper peptide forms a native-like triple stranded coiled coil in solution," *Protein Eng*. 11:1051-1055, 1998.
Walshaw and Woolfson, "Extended knobs-into-holes packing in classical and complex coiled-coil assemblies," *J. Struct. Biol*. 144:349-361, 2003.
Wang et al., "Hybrid hydrogels assembled from synthetic polymers and coiled-coil protein domains," *Nature* 397:417-420 1999.
Weiss, "HIV-1 gp41: Mediator of Fusion and Target for Inhibition," *AIDS Rev*. 5:214-221, 2003.
Wolf et al., "MultiCoil: A program for predicting two- and three-stranded coiled coils," *Protein Sci*. 6:1179-1189, 1997.
Woolfson, "The Design of Coiled-Coil Structures and Assemblies," *Adv. Protein Chem*. 70:79-112, 2005.
Yin et al., "Structure of the parainfluenza virus 5 F protein in its metastable, prefusion conformation," *Nature* 439:38-44, 2006.
Yu, "Coiled-coils: stability, specificity, and drug delivery potential," *Adv. Drug Deliv. Rev*. 54:1113-1129, 2002.
Zhao et al., "Structural characterization of the human respiratory syncytial virus fusion protein core," *Proc. Natl. Acad. Sci.* USA 97:14172-14177, 2000.
Zhu et al., "Crystal structure of human GGA1 GAT domain complexed with the GAT-binding domain of Rabaptin5," *EMBO J.* 23:3909-3917, 2004.
International Preliminary Report on Patentability for PCT/EP2008/061886, completed Oct. 26, 2009.
International Search Report for PCT/EP2008/061886, completed Feb. 27, 2009.
Written Opinion for PCT/EP2008/061886, completed Feb. 27, 2009.
Pending claims for U.S. Appl. No. 13/133,309 (dated Jun. 7, 2011).
Pending claims for U.S. Appl. No. 13/382,647 (dated Jan. 6, 2012).

* cited by examiner

NON-NATURAL PROTEINACEOUS SCAFFOLD MADE OF THREE NON-COVALENTLY ASSOCIATED PEPTIDES

CROSS-REFERENCE TO RELATED APPLICATIONS

This application is the national stage of International Application No. PCT/EP2008/061886, filed Sep. 8, 2008, which claims the benefit of U.S. Provisional Application No. 60/970,607, filed Sep. 7, 2007.

REFERENCE TO A SEQUENCE LISTING

The present application contains a Sequence Listing which has been submitted in ASCII format via EFS-Web and is hereby incorporated by reference in its entirety. Said ASCII copy, created on Sep. 24, 2012, is named 50653_004001_Amended_Sequence_Listing.txt and is 6,373 bytes in size.

FIELD OF THE INVENTION

The present invention is in the field of molecular biology and is related to a non-natural and thermodynamically stable proteinaceous (or protein) scaffold consisting of three non-covalently associated peptides. This scaffold, presenting possible therapeutic, diagnostic or purification purposes, can be used in the field of drug discovery, analytical research, purification technology and as a model for improving research and development of proteinaceous scaffold structures.

BACKGROUND OF THE INVENTION

Molecular compounds that are able to bind proteinaceous target molecules, such as flexible peptides in solution, peptides immobilized onto a solid support, linear peptide fragments in a protein, or folded proteins have a broad spectrum of possible applications. For example, they are inherently suited to be used as therapeutic compounds (e.g., inhibitors), detection probes (e.g., detection of a recombinant protein) and purification probes (e.g., in affinity chromatography). In view of the continuous evolution in these areas, there is an ongoing need for new compounds that can bind specific target molecules.

SUMMARY OF THE INVENTION

Proteinaceous (protein-like) molecular compounds may fold into triple-stranded, parallel, alpha-helical coiled coil complexes in solution. Such complexes can be very stable and are tolerant to amino acid substitutions. Accordingly, they meet the basic requirements of a protein-based scaffold. Protein-based scaffold molecules are often considered as the 'next-generation' class of compounds for molecular recognition, which increasingly compete with immunoglobulin-based compounds. Compounds of the present invention offer an alternative approach to immunoglobulins, and an additional type of protein-based (proteinaceous) scaffold.

Coiled coil complexes have found various applications in the medical and biotechnological fields (e.g., as gene regulators, antibody stabilizers, anticancer drugs, purification tags, hydrogels). The usage of two-stranded coiled coil scaffolds has been proposed for the construction of combinatorial libraries and for vaccine design. However, the present invention does not relate to two-stranded coiled coils, nor to combinatorial libraries, nor to vaccine design. Instead, the compounds of the present invention are triple-stranded coiled coils; all scaffold molecules used to date are single-stranded or, exceptionally, two-stranded. The triple-stranded alpha-helical coiled coil scaffold of the invention further shows a unique feature: it possesses a highly designable groove in between each pair of interacting alpha-helices. The present invention discloses that the latter feature makes this type of scaffold well-suited for binding to peptidic target compounds. Since the development of peptide-binding molecules is generally known as a difficult problem, the present invention discloses a valuable, innovative and non-obvious alternative to existing approaches.

The present invention is related to a non-natural, thermodynamically stable, proteinaceous scaffold consisting of three non-covalently associated peptides, wherein each peptide comprises less than 50 amino acid residues and wherein at least 50%, 55%, 65%, 70%, 75% of the said residues are substitutable into at least 10 different amino acid residue types.

Preferably, the proteinaceous scaffold of the present invention consists of three peptide sequences, wherein each peptide sequence comprises between 2 and 7 consecutive heptad repeats of the formula cxxcxxx (SEQ ID NO: 10), wherein the characters "c" and "x" denote respectively "core" and "non-core" amino acid residues and wherein the said peptide sequences have the following cumulative properties:

a) at least 50% of the c-residues are isoleucine (ILE) amino acid residues, the remaining c-residues being natural or non-natural amino acid residues other than isoleucine (ILE) and proline (PRO);
b) each x-residue is an alanine (ALA) amino acid residue;
c) the said peptide sequences associate into trimers by way of their heptad repeats forming triple-stranded, parallel, alpha-helical coiled coils wherein the said c-residues form the core;
d) (possibly) the coiled coil-forming peptide sequences remain associated under physical conditions that are different from physiological conditions being a pH of 7, a temperature of 37° C. and an ionic strength of 0.15 molar; and
e) (possibly) each x-residue is substitutable into at least 10 different amino acid residue types.

Advantageously, one or more of the c-residues are amino acids selected from the group consisting of valine, leucine, methionine, phenylalanine, tyrosine, tryptophan, histidine, glutamine, threonine, serine, alanine or glycine (or a derivative thereof) or, alternatively, from the group consisting of valine, leucine or methionine (or a derivative thereof).

Preferably, at least 70%, or, alternatively, at least 90% or, alternatively, all, or all except one, of the c-residues are isoleucines.

Advantageously, the peptide sequences remain associated under physical conditions that differ by at least two pH units (preferably four pH units), 20° C. (preferably 40° C.) and/or a factor two (preferably a factor four) in ionic strength from the physiological conditions being a pH of 7, a temperature of 37° C. and an ionic strength of 0.15 molar.

The invention further discloses embodiments wherein these peptide sequences comprise two consecutive heptad repeats having the amino acid sequence of SEQ ID NO:1: IAAIAAAIAAIAAA or, alternatively, SEQ ID NO:2: IAAIQKQIAAIQKQ, or SEQ ID NO:3: IAAIAAAIAAIAAAIAAIAAA, or SEQ ID NO:4: IAAIQKQIAAIQKQIAAIQKQ.

The invention further discloses embodiments wherein the peptide sequences comprise either the amino acid sequence SEQ ID NO:1:IAAIAAAIAAIAAA or SEQ ID NO:2:

IAAIQKQIAAIQKQ or SEQ ID NO:3:IAAIAAAIAAIAAAIAAIAAA or SEQ ID NO:4:IAAIQKQIAAIQKQIAAIQKQ, preferably the latter amino acid sequences further being substituted at one or more of the x- and/or c-residues.

The invention further discloses embodiments wherein these peptides sequences bind to a non-immunoglobulin target compound, said binding being characterized by a dissociation constant Kd lower than 1000 micromolar, preferably lower than 100 micromolar, more preferably lower than 10 micromolar or lower than 1 micromolar.

The invention is also related to a method for obtaining the scaffold of the invention, the said method comprising the following steps:

a) designing a specific amino acid sequence for the said peptides by applying the following rules:
   i. the said amino acid sequence comprises consecutive heptad repeats of the formula cxxcxxx (SEQ ID NO: 10), the characters "c" and "x" refering to "core" and "non-core" amino acid residues, respectively;
   ii. the number of consecutive heptad repeats is an integer number in the range 2 to 7;
   iii. at least 50% of the C-residues are isoleucine amino acid residues, the remaining C-residues being natural or non-natural amino acid residues other than isoleucine and proline; and
   iv. each x-residue is an alanine amino acid residue;
b) producing the designed peptides by chemical synthesis;
c) demonstrating that the designed and produced peptides, when brought into solution, associate into timers by way of their heptad repeats forming triple-stranded, parallel, alpha-helical coiled coils, and wherein the C-residues constitute the core; and demonstrating that the coiled coil-forming peptides remain associated under physical conditions that are different from physiological conditions being a pH of 7, a temperature of 37° C. and an ionic strength of 0.15 molar.

DETAILED DESCRIPTION OF THE INVENTION

Non-covalent interactions of proteins with other molecules are at the basis of all biological processes. These interactions determine the strength and specificity of molecular recognition events. Accordingly, rational application of the principles behind such interactions, in combination with biotechnological methods, may provide a means to interfere (intervene) with biological processes, or enable detection or purification of compounds of interest.

The present artificial (non-natural, designed), stable (stably folded, stably associated) scaffold molecules are composed of exactly three individual, non-covalently associated peptide fragments.

The minimal requirement for such scaffolds (complexes, peptidic associations, also referred to, in more general terms, as molecular compounds) is to assume a stable (thermodynamically stable, thermally stable, chemically stable, pH-insensitive) three-dimensional fold (3-D fold, 3-D structure).

However, particular amino acids (amino acid residues, residues) can be substituted (mutated, changed, varied) without compromising the essential properties of the scaffold, i.e., a high stability and preservation of its three-dimensional structure.

Scaffold molecules of the invention can be mutated so as to allow them to bind (bind to, bind with) specific target molecules, but one can exactly identify which amino acid residues can (and which cannot) be varied for this purpose.

The scaffold molecules (molecular compounds) of the invention are able to interfere with (influence, modify) biological processes through impeding (blocking, inhibiting) natural chemical reactions or natural molecular recognition events, or through creation of non-natural molecular recognition events. Some aspects of the present invention relate to methods to generate or optimize such compounds possibly to detect molecular compounds of interest in a study sample and possibly to isolate molecular compounds of interest from this study sample.

Instances of biological interference include, without limitation, blocking of human receptors, binding to pathogenic species, and binding to disease- or disorder-related proteins. Such type of biological interference is typically intended to curate severe diseases or disorders. These applications belong to the field of therapeutic research and development.

Current therapeutic treatments are generally based on pharmacological or biotechnological compounds, the latter including either immunoglobulin(-derived) or non-immunoglobulin compounds. The production, purification, testing and optimization of both types of biotechnological compounds is generally labor-intensive, riskful and expensive. Accordingly, there is a need for new biotechnological compounds with specific biological activity, as well as improved methods for the production, purification, testing and optimization of such compounds.

Instances wherein specific probe molecules (probes) are applied to detect the presence of an analyte of interest (target analyte) in a given sample of interest (study sample), include, without limitation, experimental analyses of samples of human, animal, plant, bacterial, viral, biotechnological or synthetic origin. Such samples typically contain biomolecules (e.g., polypeptides, polynucleotides, polysaccharides, hormones, vitamins or lipids, or derivatives thereof) that can interact specifically with a selected probe molecule. The latter interaction typically gives rise to a characteristic (e.g., spectroscopic or radioactive) signal, indicative of the presence of said target analyte in this study sample. These applications belong to the field of analytical research and development.

The number of combinations of different types of probes and targets that are effectively used in medical and biotechnological applications is virtually unlimited. In view of the continuous evolution in these areas, there is an ongoing need for new analytical tools (e.g., probes) with desired physicochemical properties (e.g., specificity, affinity, stability, solubility), as well as improved methods for the production, purification, testing and optimization of such compounds.

Instances wherein specific ligand molecules (ligands) are applied to retain (extract, isolate, purify, filter) other molecules of interest (targets, target analytes) in a given sample of interest (crude sample) include, without limitation, samples of human, animal, plant, bacterial, viral, biotechnological or synthetic origin containing biomolecules (e.g., polypeptides, polynucleotides, polysaccharides, hormones, vitamins or lipids, or derivatives thereof) that can interact (associate) with high specificity with selected ligand molecules, where the latter are separated, or can be separated, from the crude sample (e.g., by attachment onto a solid support or by precipitation), for the purpose of co-separating the target molecules from the crude sample. These applications belong to the field of purification technology.

More specific examples of purification methods include affinity chromatography and immunoprecipitation. In view of the continuous evolution in these areas, there is an ongoing need for new ligands for purification with desired physicochemical properties (e.g., specificity, affinity, stability, solubility), as well as improved methods for the production, purification, testing and optimization of such compounds. Immunoglobulin molecules (antibodies, including homologs and derivatives) are widely used in all of the aforementioned fields. They can recognize a diverse repertoire of target antigens and bind with great specificity. However, they suffer from many disadvantages including (i) the requirement of laboratory animals for the production of polyclonal antibodies (immunization technology), (ii) the requirement of complicated methods to derive monoclonal antibodies from polyclonal ensembles (hybridoma technology), (iii) the non-human nature of antibodies obtained through immunization of animal vertebrates (causing potential problems related to immunogenicity), (iv) difficulties to convert non-human antibodies into human or humanized variants (e.g., causing affinity loss), (v) alternative production methods based on protein library display and selection usually do not yield high-affinity products, thereby requiring additional affinity enhancement steps, (vi) all production methods are time-consuming and require highly specialized researchers, (vii) standard immunoglobulins may experience steric difficulties to reach their target binding sites in vivo, as opposed to in vitro test systems, (viii) native and, to a lesser extent, engineered antibodies may have suboptimal properties relating to hydrophobicity, immunogenicity, bivalency or effector function, (ix) therapeutic antibodies must be stored at near freezing temperatures, (x) immunoglobulin products are generally digested in the gut and must therefore be administered via injection or infusion, (xi) antibodies experience difficulties to permeate the blood-brain barrier.

Accordingly, there is a need for alternative, non-immunoglobulin compounds that have similar qualities but fewer weaknesses. The present invention contemplates the use of a specific type of protein (proteinaceous) scaffold and corresponding specific molecular compounds with binding specificities comparable to those of immunoglobulins, but with a totally distinct composition and structure, and lacking some of the immunoglobulins' weaknesses.

The term 'scaffold' is used within the context of the present invention to denote 'a specific, conformationally (structurally) and thermodynamically (thermally and chemically) stable proteinaceous (protein-like or protein) molecule with a specific, fixed (invariable, invariant) three-dimensional (3-D, tertiary) structure (spatial arrangement of constituting elements) consisting of one or more protein or proteinaceous polypeptide chains, the said structure being demonstrably tolerant to a variety of single and multiple amino acid substitutions at a variety of amino acid residue positions', where 'tolerant' is to be understood in the sense that the integrity (correctness) of the structure remains essentially unaltered upon performing said amino acid substitutions.

Non-immunoglobulin protein-based (proteinaceous) scaffold molecules are considered in the field as a 'next-generation' class of compounds for molecular recognition. They are mostly derived from natural protein molecules which have been selected on basis of preferred physico-chemical properties and available experimental data. Examples of this class of compounds are listed in [Hosse et al. Protein Sci 2006, 15:14-27]. Protein-based scaffold molecules consist of a stable framework structure (scaffold structure) and one or more regions that can be varied by amino acid substitution (variable regions) without compromising folding of the framework. Skerra [J Mol Recognit 2000, 13:167-187] describes some generally preferred features of protein-based scaffolds: "According to practical demands they should be based on monomeric and small polypeptides which are robust, easily engineered, and efficiently produced ( . . . )". Since all embodiments of the present invention relate to triple-stranded (3-stranded, trimeric) polypeptide complexes, and not to monomeric polypeptides, the subjects of the present invention form non-obvious instances of protein-based scaffolds. At present, the usage of triple-stranded complexes as scaffold molecules with a stable framework structure and one or more regions that can be varied by amino acid substitution has not been described, nor anticipated, nor claimed.

Because of the usually high stability of protein-based scaffold structures, large libraries (scaffold-based libraries, scaffold libraries) of molecules with essentially the same tertiary structures and slightly different sequences can be constructed. Alternatively, surface residues can be varied by rational or semi-rational protein engineering methods.

Appropriate selection methods can be applied for the purpose of identifying variants (scaffold derivatives, specific molecular compounds) with highly desired binding properties (e.g., affinities and specificities) similar to immunoglobulins. Protein-based scaffold molecules have been ascribed numerous advantages over immunoglobulins including, for example, their relatively small size, high structural stability and absence of post-translational modifications. These features considerably facilitate their synthesis, purification and storage. Moreover, high-affinity compounds can be generated without the need to proceed via an immunization step.

Certain disadvantages of protein-based scaffold structures have been reported as well, notably their premature stage of development and lack of broad validation. Further, because of their low molecular weight, they are generally cleared rapidly from the bloodstream. It can also be argued that scaffold-based proteins, especially the ones derived from non-human proteins, pose a risk to elicit strong immunologic responses. Next, their small sizes put certain limits to their 'engineerability': often only isolated surface loops are amenable to variation, which significantly restricts the number of displayed (displayable) 3-D patterns. Of particular relevance to the present invention is the fact that very few scaffold-based molecules are able to bind peptide ligands [Hosse et al. ibid]. Accordingly, there is a need for novel protein-based scaffold molecules with enhanced properties. There is a particular need for such type of molecules which can recognize small peptides.

One aspect of the present invention relates to a particular type of protein-based scaffold that is relatively insensitive to substitution of surface residues and standard protein engineering actions. Another aspect relates to scaffold-derived compounds, including compounds that tightly bind peptides comprising a sequence pattern of interest.

Yet another aspect relates to scaffold-derived compounds, including compounds that tightly bind proteins comprising a surface pattern of interest. All embodiments of the present invention relate to a specific type of protein structure (fold) that has so far not been exploited as a highly mutatable scaffold.

Synthetic peptides form a distinct class of non-natural biomolecules that are useful (used) to generate high-affinity and high-specificity binders to selected target molecules. Their main difference with scaffolds resides in the fact that they do not have (are not intended to have) a stably folded tertiary structure. Instead, synthetic peptides are a priori considered (conceived) as conformationally flexible polypeptide chains adopting innumerable transient structures in solution. While this property can be advantageously exploited (i.e., each peptide represents a myriad of possible binding structures), the conformational rigidification upon binding to a target molecule often presents a large, adverse contribution to the affinity. The loss of conformational freedom upon binding involves an entropic cost that is grossly proportional to the logarithm of the fraction of non-binding vs. binding structures. Hence, the property of conformational flexibility can be both an advantage and a disadvantage.

Thus, libraries of synthetic peptides can be applied, with variable success, to screen for small peptidic compounds with desired binding properties. Examples of flexible synthetic peptides include, without limitation, random or semi-random (biased) peptide libraries that are fused (covalently attached) to the N- or C-terminus of a selected carrier protein, peptides known as aptamers (i.e., peptides discovered through a genetic selection technique), variable heavy chain CDR3-derived peptide libraries, crypteins (i.e., peptides derived from proteolytic fragments of natural proteins), partially (locally) constrained peptide libraries (e.g., through a pair of disulfide-bonding cysteines), and the like. Peptides (and libraries thereof) that are inserted as loops (i.e., via both their termini) into a scaffold structure of choice, are herein considered as belonging to the class of scaffold-based compounds described supra; when such peptides are excised (extracted, isolated) from their scaffold context, they are again considered as free, synthetic peptides. Of specific relevance to the present invention is the fact that synthetic peptides lack the conformational restraints exerted by protein frameworks (e.g., scaffold structures). Accordingly, the present invention only remotely relates to the class of synthetic peptides. While all embodiments of the present invention do relate to synthetic (artificial, non-natural) peptides, the peptides forming objects of the present invention demonstrably fold into a specific, well-defined tertiary structure, this property allowing to distinguish them from conformationally flexible peptides and partially (locally) constrained peptides.

The alpha-helical (alpha-helical) coiled coil forms a special type of 3-D structural framework (structural motif, fold). The coiled coil fold occurs in a wide variety of proteins including motor proteins, DNA-binding proteins, extracellular proteins and viral fusion proteins [Burkhard et al. Trends Cell Biol 2001, 11:82-88]. It has been estimated that 3 to 5% of all amino acids in natural proteins are part of a coiled coil structure [Wolf et al. Protein Sci 1997, 6:1179-1189]. Coiled coils have been functionally characterized as folding (assembly, oligomerization) motifs, i.e., formation of a coiled coil structure drives in many instances the non-covalent association of different protein chains. Coiled coils have been structurally characterized as 2-, 3-, 4- or 5-stranded assemblies of alpha-helices arranged in parallel, anti-parallel or mixed topologies [Lupas Trends Biochem Sci 1996, 21:375-384 The helices are slightly wrapped (coiled) around each other in a left-handed manner, termed supercoiling. Alpha-helical coiled coils have been further characterized at the level of their amino acid sequences in that each helix is constituted of a series of heptad repeats. A heptad repeat (heptad unit, heptad) is a 7-residue sequence motif which can be encoded as HppHppp (SEQ ID NO: 11), and wherein each H represents a (potentially different) hydrophobic residue (mostly Leu, Ile or Val) and each p is a (potentially different) polar residue (e.g., Ser, Thr, Asn, Gln, Asp, Glu, His, Arg or Lys). Occasionally (infrequently), p-residues are observed at H-positions, and vice versa. Coiled coils have been thermodynamically characterized as follows. When the sequence folds into an alpha-helix, the hydrophobic residues (H) form a hydrophobic seam, whereas the polar residues (p) form a polar face. The hydrophobic seams of different alpha-helices, when associated into a coiled coil, form a central hydrophobic core (center, interior, inner part). Formation of this core, in combination with orientation of the polar faces toward solvent, is assumed to provide the main thermodynamic driving force required for stable association, although certain non-core residues may enhance stability as well.

The present invention also relates to polypeptide sequences (polypeptides, peptides, peptide fragments, peptide chains) presenting some properties as the full length molecules of the invention comprising multiple heptad repeat motifs. These embodiments further relate to triple-stranded (3-stranded, trimeric), parallel, alpha-helical coiled coil structures, preferably to stable association of the polypeptide chains in 3-stranded parallel alpha-helical coiled coil structures and to coiled coils for which the core residues provide the main driving force for stable association.

Alpha-helical coiled coils have found widespread applications in the medical and biotechnological fields. They have been exploited to function as temperature-sensing gene regulators [Naik et al. Biosens Bioelectron 2001, 16:1051-1057], antibody stabilizers [Arndt et al. J Mol Biol 2001, 312:221-227], anticancer drugs [Moitra et al. Genes Dev 1998, 12:3168-3181], purification tags [Müller et al. Methods Enzymol 2000, 328:261-282], hydrogels [Wang et al. Nature 1999, 397:417-420] and linker systems [Ryadnov et al. J Am Chem Soc 2003, 125:9388-9394] [reviewed in Mason and Arndt ChemBioChem 2004, 5:170-176].

Despite the facts that (i) the technological versatility of helical coiled coils has been acknowledged, and proven, in a variety of different applications, and (ii) the concept of drug design based on scaffolds other than helical coiled coils has proven successful in a number of cases, few, if any, examples of successful alpha-helical coiled coil scaffold-based drugs have been reported so far in the literature.

U.S. Pat. No 5,824,483 has claimed the usage of a combinatorial library of conformationally restricted peptides, wherein the said peptides associate (fold) into an alpha-helical coiled coil dimer. Peptide sequences of the scaffold are designed such that they simultaneously fulfill a double role: (i) a subset of the composing amino acid residues, denoted invariant residues, is selected for (serves to) stabilize the dimeric coiled coil, this subset including both amino acid residues suitable to form the hydrophobic core (center, interior) of the coiled coil dimer, and residues that form a covalent intrachain bond (i.e., a covalent bond between residues in one of the constituting peptides, effective to stabilize that peptide in its alpha-helical conformation), and (ii) a subset of the composing amino acid residues, denoted variant residues, is selected among the solvent-exposed residues, and is varied (substituted, mutated) so as to create a unique variation of amino acid residues in the exposed region of at least one of the constituting peptides, this variation involving at least 1000 library members. Thus, the inventors essentially claimed a combinatorial library that is based on a dimeric (2-stranded) alpha-helical coiled coil scaffold.

In contrast, the present invention relate to the usage of a trimeric (3-stranded) alpha-helical coiled coil scaffold, and not to coiled coil dimers. Furthermore, none of the embodiments of the present invention, unlike the referenced invention (U.S. Pat. No. 5,824,483) includes (mentions, requires) the usage of intrachain covalent bonds other than the obvious bonds of a standard polypeptide chain.

Trimeric (3-stranded) alpha-helical coiled coils are less frequently observed in natural proteins than are dimeric coiled coils [Wolf et al. Protein Science 1997, 6:1179-1189]. Trimeric coiled coils are also less frequently used for biotechnical or medical purposes [Mason and Arndt ChemBioChem 2004, 5:170-176]. Of particular relevance with respect to the present invention is the fact that trimeric alpha-helical coiled coils so far have not been used as probes (ligands, e.g., agonists, antagonists, inverse agonists, inhibitors, detection probes, purification probes, diagnostic probes, etc.) for binding to selected target molecules. Instead, their intrinsic scaffold properties, in the sense of 'a stably folded structural unit able to carry other elements', has been exploited almost exclusively under the form of fusion constructs (fusion proteins). More specifically, trimeric coiled coil peptides were fused (covalently attached, coupled, linked) to peptides with low trimerization propensity in order to enhance trimerization [Eckert and Kim Proc Natl Acad Sci USA 201, 98: 11187-11192], or coupled to already trimeric complexes in order to further enhance stability of the complex [Yin et al. Nature 2006, 439:38-44].

The US Patent application 2003/002795 has claimed the (not conclusively demonstrated) vaccinal usage of coiled coil structural scaffolds for the purpose of generating structure-specific peptides which present (display) potentially immunogenic epitopes that are derived (copied, transferred, transplanted, grafted, spliced) from native coiled coil proteins of microbial origin. However, the presentation of potentially immunogenic epitopes is not included in the protection of the present mention and none of the embodiments of the present invention relates to coiled coil proteins of microbial origin. In addition, none of the embodiments of the present invention includes any method, methodological step, application or product relating to the field of vaccination.

Contrary to this prior art, the present invention exclusively relates to non-natural amino acid sequences. This U.S. patent application does not consider, explicitly nor implicitly, the usage of coiled coil molecules for binding to target molecules other than antibodies. In addition, this U.S. patent application exclusively considers the usage of dimeric, and not trimeric, coiled coils.

Triple-stranded alpha-helical coiled coil scaffold structures exhibiting a high thermal stability have been developed. For example, the Ile-zipper of Suzuki et al. [Protein Eng 1998, 11:1051-1055] was shown to have a melting (unfolding, transition) temperature exceeding 80° C. Similarly, Harbury et al. [Science 1993, 262:1401-1407; Nature 1994, 371:80-83] designed a GCN4-derived triple-stranded coiled coil, named GCN4-pII, which was found stable in the crystal and in solution. Further, heterotrimeric parallel coiled coils were also designed with success [Nautiyal and Alber Protein Sci 1999, 8:84-90]. The main rules for peptides to fold into trimeric parallel configurations are also grossly known [Yu Adv Drug Deliv Rev 2002, 54:1113-1129]. Dimeric coiled coils are also known to be tolerant to sequence variation (mutations) at the level of their solvent-exposed residues.

While this may suggest that the design of trimeric parallel coiled coils is relatively straightforward, many studies have reported serious difficulties. For example, a coiled coil that was designed as a parallel dimer was observed in the crystal structure as an antiparallel trimer [Lovejoy et al. Science 1993, 259:1288-1293]. Further, the requirement of a trigger sequence for enhancing the folding kinetics has been a matter of debate [Yu ibid]. In addition, the thermal unfolding process does not always follow a simple two-state mechanism [Dragan and Privalov J mol Biol 2002, 321:891-908] and the assembly (folding) process is occasionally very slow [Dragan et al. Biochemistry 2004, 43:14891-14900].

Accordingly, in view of the many unexpected results obtained by skilled researchers, it can be concluded that the design and application of triple-stranded parallel alpha-helical coiled coil molecules is absolutely not obvious. Of special relevance is the fact that all coiled coil molecules studied till now are characterized by amino acid sequences that are identical or very close to naturally occuring amino acid sequences (see all references in this paragraph). In other words, no person skilled in the field of coiled coils or other scaffolds has proposed or demonstrated that the necessary and sufficient conditions to construct stable, trimeric, parallel alpha-helical coiled coil molecules can be defined as in the specific embodiments of the present invention.

In addition, and consequently, not any person skilled in the field has proposed or demonstrated that such coiled coil molecules may be useful as scaffold molecules being tolerant to a variety of single and multiple substitutions. In addition, and consequently, not any person skilled in the field has realized or demonstrated that such coiled coil molecules may be useful as scaffold molecules that can be converted, by way of substitution of the non-core residues, into molecular compounds (ligands) that bind to target molecules of high value in the fields of therapeutics, diagnostics or purification technology.

Recent findings in the field of HIV entry have stimulated research related to the physical properties and potential applications of trimeric coiled coils. For example, the HIV-1 envelope glycoprotein (HIV-1 Env, gp160) consists of a trimeric, viral membrane-anchored complex, also termed 'spike'. HIV-1 Env spikes are displayed on the viral surface as trimers of non-covalently associated heterodimers of gp120 (SU, surface glycoprotein) and gp41 (TM, transmembrane glycoprotein). X-ray crystallography of the gp41 ectodomain, and smaller (e.g., proteolytic) fragments thereof, has revealed that gp41 can undergo large conformational transitions from a prefusion, via an intermediate (also termed 'pre-hairpin') to a postfusion structure. The proteolytically and thermally stable portion of gp41 in its postfusion state has been characterized as a 6-helix bundle with the formula $(HR1\text{-linker-}HR2)_3$, where HR1 (HR—N, N-helix, N36) represents an N-terminal alpha-helix, HR2 (HR—C, C-helix, C34) represents a C-terminal alpha-helix, and 'linker' represents a spacer fragment between HR1 and HR2. It is of specific relevance to the present invention to know that the N-helices adopt a triple-stranded alpha-helical coiled coil structure in the postfusion state. It is further of high relevance to know that the C-helices are tightly packed (bound) onto the surface of the coiled coil region of N-helices. More specifically, each C-helix is linked to the end of an N-helix via a hairpin-forming linker fragment, and binds in an antiparallel orientation onto a groove formed by two adjacent central N-helices.

Hence, the full 6-helix bundle basically consists of a central trimeric coiled coil, onto which three outer C-helices are packed. The crystallographically determined structures suggest that this type of association is highly specific [Chan et al. Cell 1997, 89:263-273]. Thermal denaturation experiments also suggest that this type of association is fairly stable [Dwyer et al. Biochemistry 2003, 42:4945-4953].

In addition, it has been shown in a variety of biochemical assays that free C-peptides (e.g., C34) can bind with high (~nanomolar) affinity to the N-helical fragments in a spike, despite the absence of any covalent link to the N-helices [Weis AIDS Rev 2003, 5:214-221]. Moreover, it has been shown in a variety of antiviral activity assays that exogenous C-peptides can act as inhibitors of viral entry (entry inhibitors, fusion inhibitors), most likely by binding to the N-helices in a spike, thereby preventing docking of the endogenous C-helices and, hence, formation of the native 6-helix bundle, the latter being a requisite for membrane fusion [Weis ibid]. Importantly, formation of a 6-helix bundle (with a central trimeric coiled coil) has also been demonstrated for a number of other viral fusion proteins, including those of human respiratory syncytial virus, Simian parainfluenza virus and Sendai virus [Zhao et al. Proc Natl Acad Sci USA 2000, 97:14172-14177; Baker et al. Mol Cell 1999, 3:309-319; Ludwig et al. EMBO J 2003, 22:3761-3771].

Aforementioned experimental findings indicate that trimeric alpha-helical coiled coils have the potential to bind to (associate with) peptidic fragments in a strong and specific manner, e.g., in a configuration wherein the bound fragments are strictly alpha-helical and/or are oriented antiparallel to the coiled coil helices and/or are tightly side chain-anchored into the grooves formed by adjacent coiled coil helices and/or are tightly hydrogen-bonded (H-bonded) to the coiled coil helices and/or make tight electrostatic interactions with the coiled coil helices.

Accordingly, the experimentally determined structures of viral fusion proteins provide a source of structural information that may be utilized in the design of trimeric alpha-helical coiled coil structures for the purpose of binding target peptides or proteins. Possible current and future embodiments of the present invention relate to designed (artificial, non-natural) trimeric alpha-helical coiled coils that are capable of binding selectively to target peptides or proteins. In one possible embodiment, such designed coiled coil constructs bind to peptide molecules, either free in solution or attached to a solid support. In another possible embodiment, such designed coiled coil constructs bind to a linear fragment in a protein; examples of the latter type of binding include, without limitation, binding to intrinsically disordered protein (IDP) fragments [reviewed in Hansen et al. J Biol Chem 2006, 281: 1853-1856], flexible protein loops or tail fragments [Dunker et al. PDB Newsletter 1997, 81:3-5], or transiently disordered protein fragments, e.g. an intermediate during a viral fusion process [Koshiba and Chan J Biol Chem 2003, 278:7573-7579]. In yet another possible embodiment, a designed coiled coil construct can bind to a folded protein, for example, a protein of known tertiary structure displaying a set of surface amino acid residues in a configuration that is structurally compatible with the surface of the designed coiled coil construct.

There are many possible technical methods to generate trimeric, parallel, alpha-helical coiled coil structures with specific, desired binding properties. Such methods may include a variety of state-of-the-art experimental and theoretical (i.e., bioinformatics and molecular modeling) methods, and combinations thereof. In principle, the majority of methods that were previously proven useful to generate target-specific immunoglobulin- or protein scaffold-derived molecules should also be useful for the design of said coiled coil structures.

In addition to these state-of-the-art methods, the following non-standard method exploits some of the characteristics that are unique to trimeric coiled coils (e.g., the availability of structural information in the Protein Data Bank, the trimeric nature of the scaffold structures, experimental data on protein fragments in association with trimeric coiled coils, and the like) and is therefore considered a preferred, though not obligatory, design method.

A method to generate a composition of artificial peptides forming subjects of the present invention includes the steps of (step 1) providing a reference 3-D structural representation of a triple-stranded, parallel, alpha-helical coiled coil complex by retrieving the corresponding atomic coordinates from the Protein Data Bank;

(step 2) providing a set of 3-D structural representations of triple-stranded, parallel, alpha-helical coiled coil complexes that are associated with additional proteinaceous elements, by retrieving the corresponding atomic coordinates from the Protein Data Bank;

(step 3) superimposing one or more of the representations of step (2) onto the representation of step (1) by applying a least-squares fitting method to a portion or all of the backbone atoms of the coiled coil regions of the representations of steps (1) and (2);

(step 4) selecting, from coiled coil regions of representations of step (2), amino acid residues that are in contact with proteinaceous chemical groups, for example, side-chain or backbone chemical groups;

(step 5) in silico grafting, by way of transferring atomic coordinates, either the entire amino acid residues selected in step (4), or only their side-chains, onto the reference 3-D structural representation of step (1), and, optionally, optimizing the conformation of the grafted amino acid residues by using a suitable molecular modeling method, for example, an energy minimization method or a molecular dynamics method;

(step 6) formulating a final composition of artificial peptides by way of synthesizing peptides having an amino acid sequence as appearing in the reference representation of step (1) being substituted into amino acid residues selected in step (4) and grafted in step (5);

(step 7) measuring the binding affinity of the composition of artificial peptides of step (6) for one or more peptides having amino acid residues that are structurally compatible with the binding surface of said artificial peptides, said measurement serving to identify true-positive and false-positive binders.

It is further specified that true-positive binders are predicted binders that are experimentally confirmed, whereas false-positive binders are experimentally disproved. As will be acknowledged by those skilled in the field of molecular modeling and, by extension, protein design, not all theoretically binding ligand molecules are in agreement with experimental results. Yet, theoretical methods (e.g., steps 1-6 of said workable method) can considerably expedite identification of true binders by formulating a limited number of potential binders that can be experimentally tested (e.g., by step 7 of said workable method).

The quantitative binding of designed molecular constructs in general, and of the artificial peptides forming subjects of the present invention in particular, is an important characteristic of said constructs and peptides. A very strong binding is is defined as a binding that is characterized by a dissociation constant (Kd) of about 1 nanomolar, good (reasonably strong) binding by a Kd of about 1 micromolar, and poor (weak) binding by a Kd of about 1 millimolar. Preferred embodiments of the present invention relate to quantitative binding characterized by Kd-values in the range 1-1000 micromolar. A practical reason for not selecting very strong binding (i.e., about 1 nanomolar) has to do with the binding specificity of said artificial peptides.

To a first approximation, binding specificity is related to binding affinity by the simple rule 'the higher the affinity, the higher the specificity' [Eaton et al. Chem Biol 1995, 2:633-638].

An important aspect of the present invention is that high binding specificity of the artificial coiled coil peptides for their target compound is not preferred and, therefore, a high binding affinity is also not a requirement. The latter is due to a number of potential applications of the present invention. For example, in an embodiment of the present invention, artificial coiled coil peptides are acquired which recognize (show detectable binding to) target molecules displaying a given surface pattern (surface motif, critical residues of a binding site). It may be advantageous that said coiled coil peptides also recognize other target molecules displaying the same, or a similar, surface pattern, this phenomenon being generally known as 'cross-reactivity' or 'cross-binding'. Cross-reactivity is one of the main consequences of low specificity and can be a favorable or unfavorable property, depending on the goal of the application.

An important application of the present invention may be to acquire artificial coiled coil peptides which show detectable cross-reactivity with a variety of target molecules. Such type of reactivity (binding, recognition) may occur through non-covalent association with a number of critical residues forming part of the target molecule surface pattern.

It may be especially advantageous if the binding primarily depends on these critical residues and not on other residues of the surface pattern. As will be appreciated by those skilled in the field, it can be expected that, in such cases, the said coiled coil peptides will have an inherent potential to recognize a variety of different target molecules that are essentially unrelated in amino acid sequence, tertiary structure and biological function. Accordingly, a preferred application of the present invention is to use artificial coiled coil peptides to screen for (detect, by way of binding to) target molecules of different nature and function, while the latter share essentially only a number of highly similar critical amino acid residues or, in general, proteinaceous chemical groups.

In applications wherein the target compound is of the format 'free peptide' or 'peptide attached (immobilized) onto a solid support' or 'linear fragment in a protein', here collectively termed 'peptidic fragment', preferred instances of critical residues are embodied by series of specific amino acid residues occurring within said peptidic fragment, such series of specific residues also being referred to as 'sequence motifs' or 'sequence patterns'. A sequence motif may be formally noted (encoded, represented) as a pseudo-amino acid sequence wherein critical residues are symbolized by standard amino acid one-letter codes, non-critical residues by "x" characters, and flanking fragments by "-" signs. For example, a specific sequence motif could be "-IxxLxxxV-" (SEQ ID NO: 12), meaning that the. "I", "L" and "V" characters represent critical isoleucine, leucine and valine residues, respectively, the "x" characters represent non-critical residues and the "-" signs represent flanking fragments; according to standard amino acid naming conventions, the mentioned sequence motif would embody all possible peptide sequences having isoleucine (I) followed by two undefined (indifferent) residues, followed by leucine (L), followed by three undefined residues, followed by valine (V).

Alternatively, a specific sequence motif may be encoded as a pseudo-amino acid sequence wherein critical residues with highly similar physico-chemical properties (e.g., aliphatic, aromatic, positively/negatively charged residues) are grouped and jointly referenced by a suitably chosen symbol. For example, a specific sequence motif of this kind could be "-axxaxxxa-" (SEQ ID NO: 13), wherein it is further specified that the characters "a" denote aliphatic residues of the set {leucine, isoleucine, valine}, this pseudo-sequence embodying all possible peptide sequences having three aliphatic residues that are spaced as specified in the motif. It is agreed that there exists a very large number of conceivable motifs, depending on the number of critical residue positions, spacings and type of grouping. Yet, it will be appreciated by those skilled in the field that the number of potentially interesting motifs is nevertheless very small compared to the total number of possible amino acid sequences of the same length.

Accordingly, any particular sequence motif comprising at least two critical residue positions at which maximally four amino acid residues are considered, and which are spaced by a fixed number of non-critical residues, can be genuinely called a specific sequence motif. Accordingly, artificial coiled coil peptides binding selectively to peptidic fragments comprising such sequence motif can be attributed a certain degree of specific binding. However, it is remarked that absolute or high specificity will generally be not aspired and will in many practical cases not even be desired.

In applications wherein the target compound is of the format 'folded protein', whether dispensed in solution or attached (immobilized) onto a solid support, here collectively termed 'protein target', preferred instances of critical residues are embodied by series of specific amino acid residues occurring at the molecular surface of said protein target, such series of specific residues also being referred to as 'surface motifs' or 'surface patterns'; a surface motif cannot be formally noted in pseudo-amino acid sequence format as it embodies a series of critical residues that are disjunct in sequence but clustered in 3-D space.

A surface motif is further specified as a set of residues at the surface of a target protein that are critical for binding, generally a subset of the residues forming the full binding site. A surface motif also bears strong similarity to antibody combining sites known in the field as conformational epitopes. Similar to peptidic target fragments, critical residues can either be single amino acid residues or groups thereof.

A surface pattern can therefore include a certain degree of diversity while still being envisaged as a specific surface motif. Accordingly, artificial coiled coil peptides binding selectively to protein targets comprising such surface motif can be attributed a certain degree of specific binding. It is also remarked in this context that absolute or high specificity will generally be not aspired and will in many practical cases not even be desired.

The notion 'critical residues' is hereinafter detailed and applies to all types of target compounds forming subjects of the present invention. Amino acid residues are generally considered as critical residues if they significantly contribute to the binding between, on the one hand, the artificial coiled coil peptides of the present invention and, on the other hand, a given target compound of interest, in other words, if they significantly contribute to the binding strength (binding affinity) of the coiled coil—target complex. The term 'critical residue', as used in this context, is strictly reserved for target residues (although it is recognized that certain residues of coiled coil peptides may also be critical for the binding).

It is extremely difficult to determine the individual contribution of individual amino acid residues to the total (global) affinity of a complex on basis of experimental or theoretical information of the complex alone. Even the most sophisticated theoretical (e.g. advanced molecular modeling) methods cannot accurately determine single-residue contributions.

However, there exists a widely accepted experimental method that is broadly applicable to map (determine) individual contributions to the overall stability of complexes (and even protein folding stability). This method makes use of point mutants, i.e., single-residue substitutions, of the original (unmodified) target compound; the original target compound is usually referred to as the 'wild type', whereas a point mutant is this same compound wherein one amino acid residue is substituted for another type of amino acid. In the main, residues are substituted for a supposedly 'neutral' amino acid.

Therefore, wild type non-alanine residues are mostly substituted into alanine, whereas wild type alanines are often substituted into glycine. This technique is commonly known as alanine-scanning (Ala-scanning). In practice, a panel of single-residue alanine-mutants (Ala-mutants) can be synthesized and the affinity of each Ala-mutant is then compared with the affinity of the wild type. Alanine-mutants showing significantly reduced affinity are indicative of the importance of the wild type amino acid at the corresponding position. Because there exist different human interpretations of what is to be considered a significant reduction in affinity, the latter is specified in a preferred way, as follows. Whenever the binding affinity of an Ala-mutant is at least a factor 10 lower (i.e., the dissociation constant, Kd, is at least a factor 10 higher) than that of the wild type compound, the corresponding wild type residue is deemed critical for the binding. Whenever the binding affinity of an Ala-mutant is at least a factor 100 lower (i.e., the Kd is at least a factor 100 higher) than that of the wild type compound, the corresponding wild type residue is deemed highly critical. In the other cases (i.e., when the affinity decreases by less than a factor 10, or when it increases), the corresponding wild type residue is deemed not critical.

Accordingly, in a preferred possible embodiment of the present invention, the critical nature of target amino acid residues is demonstrated by comparing the affinity of the unmodified target compound with the affinities of alanine point mutant compounds, or glycine point mutant compounds if the unmodified compound has alanine at the corresponding position.

In another preferred possible embodiment, specific amino acid residues of the target compound are deemed critical if the dissociation constant of the corresponding point mutant is at least a factor 10 higher than that of the unmodified target compound. In another, equally preferred possible embodiment, specific amino acid residues of the target compounds are further deemed highly critical if the dissociation constant of the corresponding point mutant is at least a factor 100 higher than that of the unmodified target compound.

In another preferred possible embodiment, binding of the same composition of artificial coiled coil peptides is demonstrated for at least two, and preferably multiple (e.g., 10) different target compounds with identical, or physico-chemically highly similar, critical amino acid residues, said demonstrated binding being indicative of a broad applicability of the same artificial coiled coil peptides for recognition of different target compounds sharing essentially only a small number of highly similar critical amino acid residues.

As will be acknowledged by those in the field of drug discovery, any newly discovered chemical or biomolecular compound showing appreciable binding to a given target compound has a certain potential to become a drug lead compound; it may be transformed into a true drug after intensive pharmacokinetic and pharmacodynamic analysis and modifications known as lead optimizations. There are two aspects in this which directly and indirectly relate to the present invention, respectively. The first is about the discovery process, and directly relates to the present invention. (The second aspect is about lead optimization and is further detailed below.) Drug lead discovery tradionally involves brute-force high-throughput screening (HTS) of large libraries of compounds. It has been argued, however, that this approach is becoming increasingly unattractive [Engels and Venkatarangan Curr Opin Discov Devel 2001, 4:275-283]. Multiple hybrid screening techniques have been suggested that unite in silico and in vitro screening in one integrated process; such hybrid approaches have been termed 'smart screening'.

An important aspect of 'smart screening' is the design of screening libraries with an improved hit rate. With respect to molecular target compounds, it would be advantageous to possess small screening libraries with a high content of potential binders. It would be most advantageous to not have to screen a library at all, but to be able to select candidate binders on basis of their previously demonstrated binding properties, for example, a demonstrated capability to bind to target molecules displaying a given sequence pattern or surface pattern. Evidently, it will be impossible to select a candidate binder if the target compound of interest displays not any sequence or surface pattern that matches with the previously demonstrated binding characteristics of compounds in possession.

Therefore, it may be most advantageous to be in possession of multiple compounds with different, demonstrated binding characteristics. Accordingly, an important possible embodiment of the present invention relates to a specific instance of smart screening. More specifically, an important possible embodiment of the present invention relates to a method for identifying a lead compound for target recognition, said method making use of a composition of artificial coiled coil peptides with known binding characteristics. Another possible embodiment of the present invention relates to a method for identifying a lead compound for target recognition, said method making use of multiple compositions of artificial coiled coil peptides with known binding characteristics, wherein each of said compositions has a unique specificity for binding to target compounds.

The second aspect relating to drug development concerns techniques for lead optimization, and relates only indirectly to the present invention. As will be acknowledged by those skilled in the field of lead optimization, the discovery of an initial binder to a particular target of interest does not necessarily imply that this binder will become a true drug. Almost invariably, initial hits have to be modified (i.e., changed in 'chemical space' for small-molecule compounds or in 'sequence and chemical space' for proteinaceous compounds) in order to improve, on the one hand, their affinity and specificity and, on the other hand, solubility, permeability and metabolic stability [Bleicher et al. Nat Rev Drug Discov 2003, 2:369-378]. Such modifications are generally performed in downstream steps of drug development processes. Correspondingly, chemical and/or structural modifications to artificial coiled coil peptides forming the subject of the present invention do not form aspects of the present invention itself.

Yet, a number of such modifications can be disclosed here to illustrate the potential of said artificial peptides to be subject to advanced engineering steps: given a composition of artificial coiled coil peptides according to the present invention, it is possible to modify said artificial peptides by any of the following, non-limiting, set of advanced engineering steps:

- these artificial peptides may be modified in amino acid sequence, thereby creating one or more derivatives thereof;
- these artificial peptides and derivatives may be modified, e.g., to enhance their stability;
- these artificial peptides and derivatives may be modified, e.g., to enhance their folding kinetics;
- these artificial peptides and derivatives may be modified, e.g., to enhance the correctness of their folded state;
- these artificial peptides and derivatives may be modified, e.g., to enhance their binding affinity to a target compound;
- these artificial peptides and derivatives may be modified, e.g., to enhance their binding specificity for a target compound;
- these artificial peptides and derivatives may be modified, e.g., to enhance their solubility;
- these artificial peptides and derivatives may be covalently linked to one another by utilizing suitable linker fragments connecting the C-terminal end of one peptide to the N-terminal end of another peptide, this covalent linkage leading to the construction of a single-chain derivative;

these artificial peptides and derivatives may be covalently linked to one another by substituting selected amino acid residues for cysteine, e.g., to stabilize their folded structure by disulfide bonds;

these artificial peptides and derivatives may be covalently linked to protein molecules, e.g., they may be incorporated in fusion proteins;

these artificial peptides and derivatives may be covalently linked to other copies of the same artificial peptides or derivatives, e.g., to increase avidity;

these artificial peptides and derivatives may be covalently linked to other artificial peptides or derivatives with different binding properties, e.g., to provide bi- or multispecificity;

these artificial peptides and derivatives may be supplied with detection tags;

these artificial peptides and derivatives may be supplied with purification tags;

these artificial peptides and derivatives may be glycosylated;

these artificial peptides and derivatives may be PEGylated;

in view of the fact that these artificial peptides and derivatives form stable and compact structures, they may be constructed or manipulated, in principle, by all techniques applicable to proteins and protein scaffolds. While many of the aforementioned handlings known in the field of protein engineering may appear either highly advanced or straightforward, depending on the level of expertise of the person confronted, none of them can be applied without taking the proper precautions. This is of particular relevance to the modification concerning the coupling of said artificial peptides by utilizing suitable linker fragments, thereby constructing single-chain derivatives.

On the one hand, such constructs would be highly desirable because they may allow production via standard molecular biological (recombinant) techniques. Furthermore, such constructs may considerably facilitate the development of coiled coils comprising asymmetric (non-identical) alpha-helical fragments, which opens the way to a variety of novel applications. The formation of the coiled coil region would not involve association of free peptides but folding of a single chain which may, or may not, be thermodynamically advantageous.

The linker fragment can also be used to supplement the scaffold structure with additional desired properties including, but not limited to, further stabilization of the construct, epitope presentation, immunological masking, crosslinking, labeling, etc. On the other hand, while all of these possibilities may be highly desirable, it is remarked that the connection of opposite (distal) ends in a protein tertiary structure is far from trivial. It is has not yet been demonstrated how long such linker fragments should be to connect the alpha-helical termini in a suitable (intended) way, e.g., to facilitate, or at least permit, association of the alpha-helical fragments with the proper spatial arrangement (handedness around the central axis). Further, it has not yet been demonstrated whether such constructs would correctly fold at all, since it is at least theoretically conceivable that incorrect associations such as antiparallel folding or interchain association or aggregation in general might be promoted. Therefore, such constructs will need to be investigated further. They do not form embodiments of the present invention, although the basic physical and technical principles are disclosed here.

Examples

Example 1

Amino Acid Sequence of an Artificial Peptide with Core and Non-Core Residues This example provides the amino acid sequence of a specific peptide forming an instance of the present invention. The amino acid sequence, AIAAIQKQIAALQKQIAAIQKQIA (SEQ ID NO: 5), is presented in single-letter notation, wherein A refers to alanine, I to isoleucine, L to leucine, Q to glutamine, and K to lysine. The peptides with this amino acid sequence fold in solution into triple-stranded, parallel, alpha-helical coiled coil complexes by way of their isoleucine and leucine amino acid residues forming a hydrophobic core (center, interior) and the other residues being oriented towards solvent. The artificial peptide comprises three heptad repeats labeled “HR1”, “HR2” and “HR3” in FIG. 1.

The FIG. 1 is a schematic representation of the amino acid sequence of an artificial peptide comprising heptad repeats (HRx), core residues (black boxes), non-core residues (gray boxes) and flanking regions (white boxes). The peptide further comprises a C-terminal heptad core residue labeled “t”. The peptide further comprises N- and C-terminal flanking fragments labeled “N” and “C”, respectively. Each heptad repeat residue is further annotated with indices “a” to “g” and a number corresponding to the heptad repeat number. Core residues are located at a- and d-positions. It is seen that 5 out of the 6 core residues of the three full heptad repeats are isoleucines. The isoleucine residue labeled “a4” belongs to the partial heptad repeat “t”.

Example 2

Figure 2:
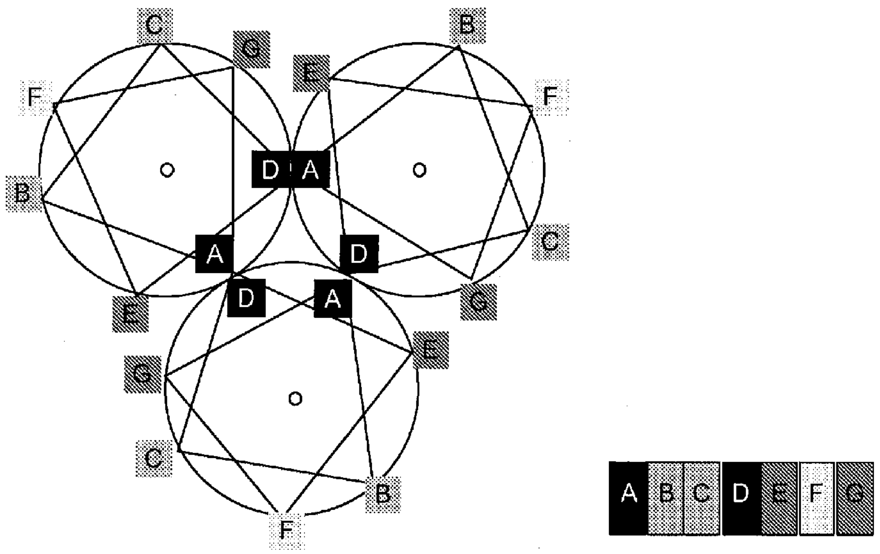

Principles of a Triple-Stranded, Parallel, Alpha-Helical Coiled Coil Complex Heptad core residues are shielded from solvent in triple-stranded, parallel, alpha-helical coiled coil complexes, as illustrated in FIG. 2. Non-covalent interactions between contacting core residues (positions A and D in FIG. 2) provide the main thermodynamic driving force for the peptides to adopt such fold. The FIG. 2 is a helical wheel representation of a triple-stranded, parallel, alpha-helical coiled coil scaffold. The left panel shows a top view on the scaffold. The right panel shows a linear sequence of heptad repeat positions. Only one heptad repeat is displayed for clarity reasons. Different shades are used to indicate specific topological positions. The non-core residues (positions B, C, E, F and G) are at least partially solvent-accessible (positions E, G less than B, C, and positions B, C less than F) and are susceptible to amino acid substitutions without (major) implications for the stability of the complex (scaffold structure).

Example 3

Alpha-Helical Structure and Reversible Folding/Unfolding

To demonstrate quantitative formation of alpha-helical secondary structure of a reference artificial peptide in solution, the inventors have synthesized the peptide with the amino acid sequence Ac-MSIEEIQKQQAAIQKQIAAIQK-QIYRMTP-NH2 (SEQ ID NO: 6) and recorded the circular dichroism (CD) spectrum. The amino acid sequence is given in single-letter code; Ac- and —NH2 mean that the peptide was acetyl-initiated and amide-terminated, respectively. This peptide is to be considered as a derivative of the reference peptide composed of the triple heptad repeat sequence (IAAIQKQ)3 (SEQ ID NO: 4), with modifications at the amino- (N-) and carboxy- (C-) terminal ends to improve the alpha-helical nature of the termini (often referred to as capping). More specifically, the flanking residues Ac-MS- were attached at the N-terminus, in combination with the substitution of two consecutive glutamic acid residues (EE) for the two alanine residues (AA) in the first heptad of the reference sequence.

Furthermore, the flanking residues -IYRMTP-NH2 (SEQ ID NO: 14) were attached at the C-terminus, such that the amino acids isoleucine (I) and methionine (M) are located at conventional heptad a- and d-positions, allowing this flanking sequence to form an extra, though incomplete, heptad. The tyrosine (Y) was introduced at a solvent-oriented b-position to enable spectrophotometric concentration determination. The arginine (R), threonine (T) and proline (P-NH2) residues were introduced to improve C-terminal helical capping. In addition, the isoleucine (I) residue at the a-position of the second heptad was replaced by a glutamine (Q) residue to force the coiled coil-forming peptides to associate in the correct (intended) way, i.e., to ascertain formation of a trimeric complex and to avoid possible heptad register shifts [Eckert et al. J Mol Biol 1998, 284:859-865].

Figure 3:
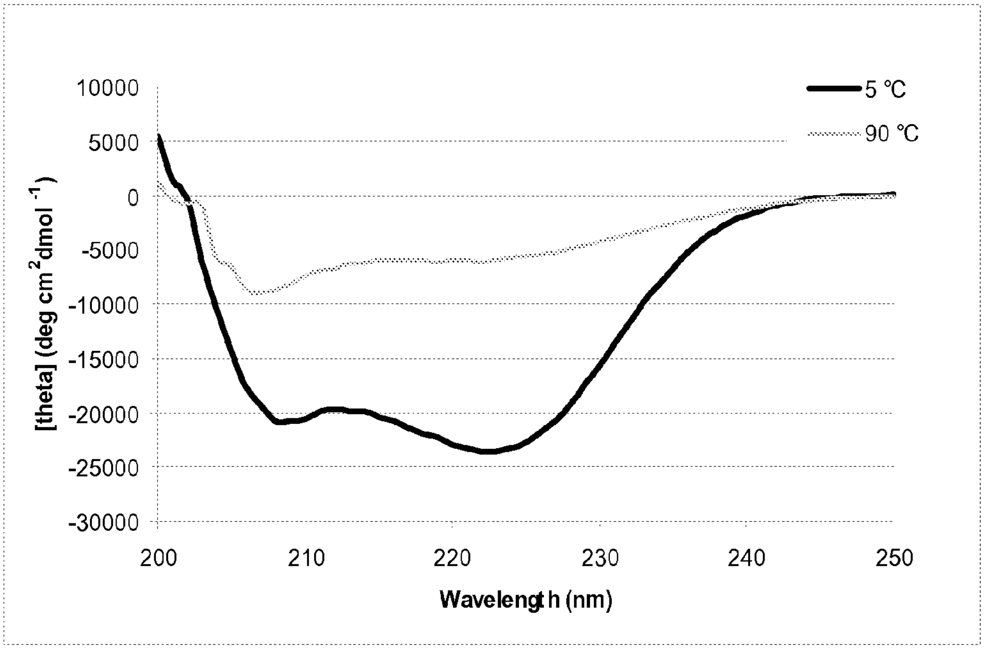

The said synthesized peptide was dissolved at a concentration of 292 microM in 20 mM phosphate buffer (PBS), 150 mM NaCl, pH 7.2. The CD spectra were measured between 200 and 250 nM, at 5 and 90 degrees Celsius (FIG. 3). The spectrum at 5 degrees Celsius was indicative of a high alpha-helical secondary structure content, in agreement with the expectation that all heptad regions, but not all of the flanking residues, would assemble as alpha-helical coiled coils. The spectrum at 90 degrees Celsius showed that the alpha-helical structure was greatly, but not completely, lost at elevated temperatures.

Figure 4:
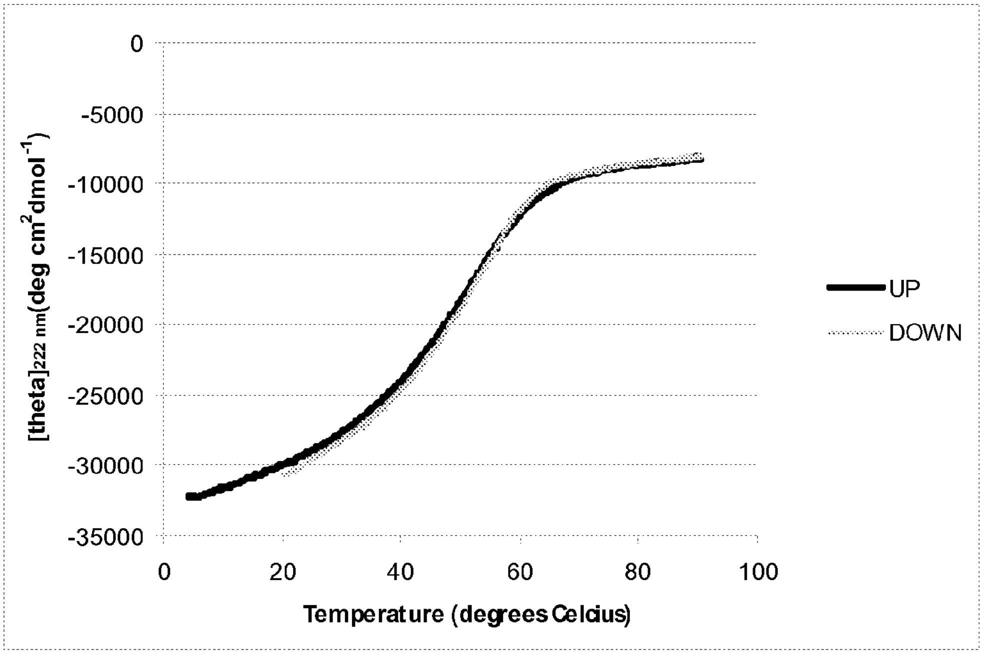

To analyse whether the temperature-induced transition between helical and nonhelical states was reversible, a forward (up) and backward (down) thermal scan was performed on the same sample, by recording the CD signal at 222 nM as a function of temperature at a scanning rate of about 1 degree Celsius per minute (FIG. 4). It was observed that the up and down scans almost perfectly coincided, thereby confirming the quantitative unfolding and refolding of the peptides in the sample.

It was further analyzed whether the thermal unfolding curve of FIG. 4 conformed to the thermodynamic equations describing the equilibrium folding/unfolding reaction between three molecules free (monomeric) peptide and one entity of folded (trimeric) complex. This reaction is generally written as 3 peptide <=> $\text{peptide}_3$ wherein "<=>" refers to a chemical equilibrium, "peptide" to a monomeric peptide in solution and "$\text{peptide}_3$" to a trimeric entity in the folded (assembled, associated) state. This thermal unfolding curve was fitted to the theoretic equations:

$$\theta(T) = \theta_M(T) + (\theta_T(T) - \theta_M(T)) \left(1 + \sqrt[3]{F\left(-\frac{1}{2} + \sqrt{\frac{1}{4} + \frac{F}{27}}\right)} + \sqrt[3]{F\left(-\frac{1}{2} - \sqrt{\frac{1}{4} + \frac{F}{27}}\right)}\right)$$

wherein

-continued $$F = \frac{\exp\left(-\frac{\Delta H_t}{RT}(1 - T/T_t) - \frac{\Delta C_p}{RT}(T - T_t - T\ln(T/T_t))\right)}{4}$$

and

Figure 5:
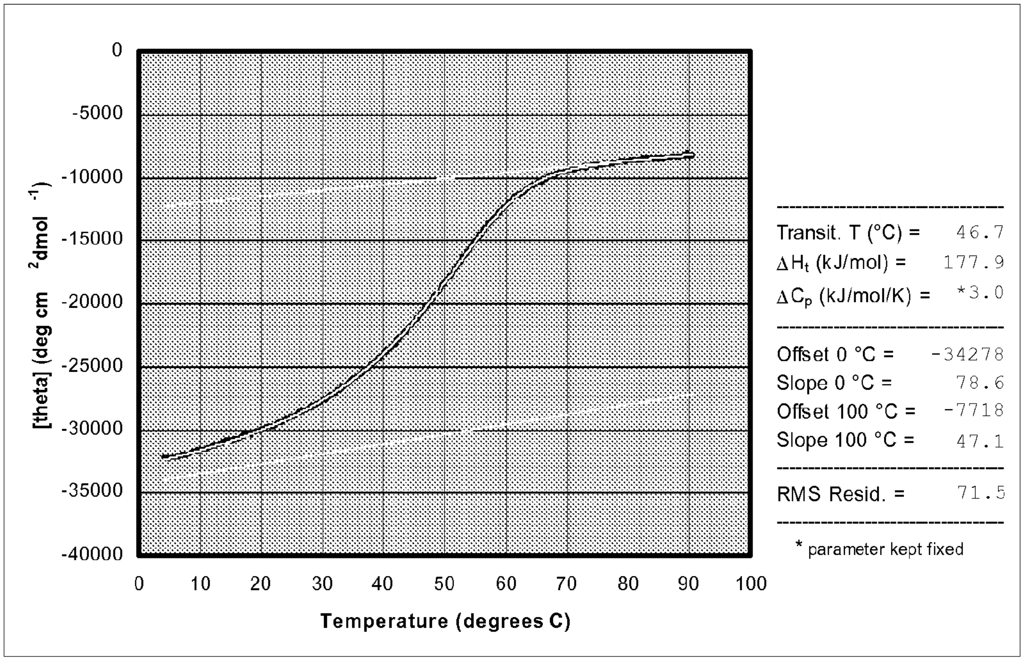

T≡the temperature, in degrees Kelvin, of the sample

θ(T)≡the CD-signal $[\text{theta}]_{222\ nm}$, in deg $cm^2$ $dmol^{-1}$, as a function of T $\theta_M$(T)≡the CD-signal for 100% free (monomeric) peptide as a function of T $\theta_T$(T)≡the CD-signal for 100% associated (trimeric) peptide as a function of T $T_t$≡the transition temperature, where 50% of the total peptide concentration is associated $\Delta H_t$≡the enthalpy difference, in kJ per mole peptide, between mono- and trimeric states $\Delta C_p$≡the heat capacity difference, in J $mol^{-1}$ $K^{-1}$, between mono- and trimeric states R≡the ideal (universal) gas constant≡8.31 J $mol^{-1}$ $K^{-1}$ The results of this fitting operation are shown in FIG. 5. It was found that the theoretic curve almost perfectly coincided over the entire temperature range with the experimental curve, thereby confirming trimeric association of the peptides.

FIG. 5 represents fitting of a theoretic equation for trimeric association to experimental data. The experimental data are taken from FIG. 4, curve labeled "UP". The theoretic equations used are listed supra. The fitted parameters (fitting results) are listed at the right in FIG. 5. "Transit. T" corresponds to $T_t$, but is expressed here in degrees Celsius. The parameter "delta $C_p$" was kept constant at 3.0 kJ $mol^{-1}$ $K^{-1}$. The parameters "$\text{theta}_M$(T)" and "$\text{theta}_T$(T)" were treated as linear functions of T, resulting in the white straight lines described by the respective offsets and slopes indicated at the right in the figure. "RMS Resid." refers to the root-mean-square of the differences between experimental and theoretic data points. The fitted (theoretic) curve itself is plotted in white on the figure and coincides over the entire temperature range with the experimental data points shown in black.

Example 4

Usage of All-Isoleucine Core Residues

To analyse whether the glutamine residue at position a of the second heptad in the reference peptide of Example 3 (SEQ ID NO: 6) was required for correct (intended) folding into a trimeric coiled coil, this residue was replaced by isoleucine, resulting in a peptide named "Q2aI" having a sequence with isoleucine at all core positions (except methionine within the C-terminal flanking fragment). For this purpose, the peptide with the following sequence was synthesized: Ac-MSIEEIQKQIAAIQKQIAAIQKQIYRMTP-NH2 (SEQ ID NO: 7).

Figure 6:
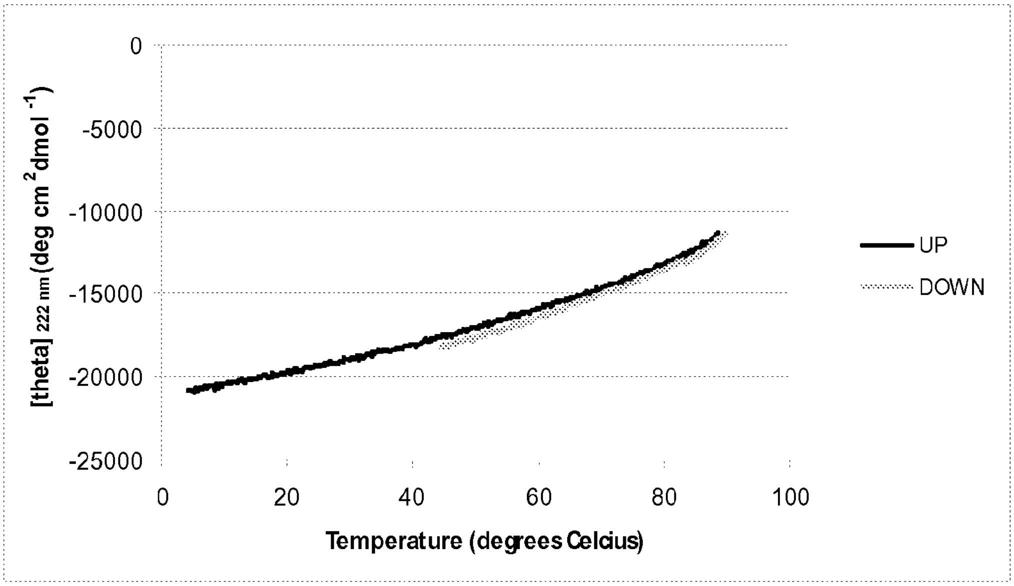

FIG. 6 shows the thermal denaturation curve for a sample preparation of the Q2aI peptide under the same conditions as in Example 3. The global CD signal was somewhat lower than expected, which could be due to an instrumental deviation, an error in the concentration determination, a lower purity, or a lower than expected alpha-helical content. Nevertheless, the main goal of this experiment was to examine the effect of the glutamine-to-isoleucine mutant on the stability of the complex. It was therefore interesting to find that this variant showed extremely high resistance against thermal denaturation, i.e., it was extremely thermostable. The estimated transition temperature was around 97 degrees Celsius, although the latter was difficult to determine because of incompleteness of the transition. Also, the down-scan showed full recovery of the CD signal, indicating full reversibility.

Figure 7:
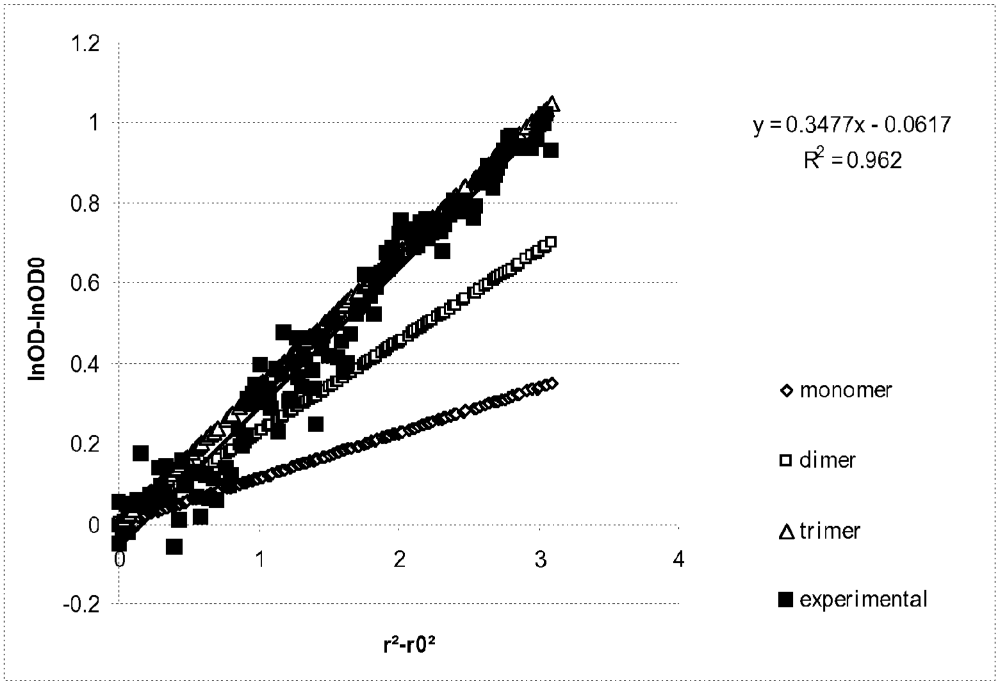

To confirm that the assembled complex had the correct molecular weight (MW), as expected for a trimer, the Q2aI peptide was submitted to analytical sedimentation equilibrium ultracentrifugation at 25000 rpm at a concentration of approximately 1 mg/ml. FIG. 7 shows the linearized optical density (OD) curve in comparison with the theoretical curves for monomeric, dimeric and trimeric complexes. It was found that the experimental data points coincided very well with the trimeric model curve. From the slope of the linear regression line, the apparent molecular weight of 10500 Da was derived, in good agreement with the theoretic value of 10242 Da (3 times the MW of 3414 Da for a monomer).

Figure 8:
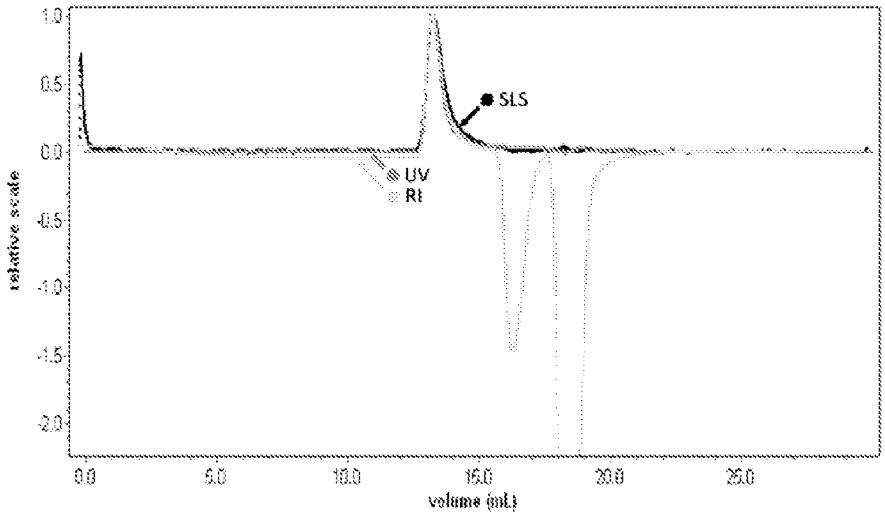

To further confirm formation of trimeric complexes, the same Q2aI peptide was also analyzed by static light scattering. 200 microliter peptide at 1 mg/ml in PBS was put on a Superdex 75 10/300 GL gel filtration column connected to ultra-violet (UV), refractive index (RI) and static light scattering (SLS) detectors. FIG. 8 shows the results. The signals (curves) from the three different detectors are labeled accordingly. A well-shaped light scattering peak was observed coinciding with a UV and RI peak. The apparent molecular weight derived for the UV peak was 12530±1510 Da, again in good agreement with the expected value.

It was concluded that the usage of all-isoleucine core residues did not have an adverse effect on the assembly of the peptide into trimers, as could be expected on basis of theoretic considerations about potential (unintended) heptad register shifts. Instead, all tests indicated the proper and exclusive folding into trimers with the correct (expected) molecular weight. Furthermore, this all-isoleucine core peptide had a very high thermal stability, for it did not quantitatively unfold up to 95 degrees Celsius. Therefore, this peptide can be considered as a preferred trimeric coiled coil-forming scaffold peptide.

Example 5

Analysis of Core Mutants

Figure 9:
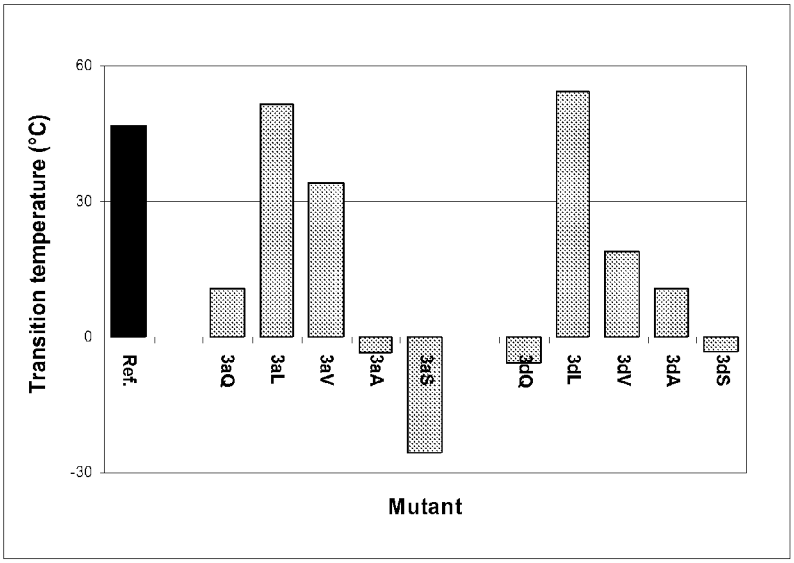

To further analyse the tolerance of the trimeric coiled coil scaffold towards amino acid residue substitutions at specific core positions, the following mutants of the reference peptide examined in Example 3 (i.e., the one comprising a glutamine at position 2a (SEQ ID NO: 6), not the more stable Q2aI mutant of Example 4 (SEQ ID NO: 7)) were synthesized: 3aQ, 3aL, 3aV, 3aA, 3aS, 3dQ, 3dL, 3dV, 3dA and 3dS, wherein each time “3” refers to the third heptad and “a” and “d” refer to a- and d-positions, respectively; the letters Q, L, V, A and S refer to mutations into glutamine, leucine, valine, alanine and serine, respectively. All ten peptides were analyzed by thermal CD scanning as in Examples 3 and 4. Fitting of the thermal denaturation curves, as described in Example 3, gave the corresponding transition temperatures shown in FIG. 9. It was found that, compared to the reference peptide comprising isoleucine at positions 3a and 3d, only leucine had a slightly stabilizing effect at both the a- and d-positions (3aL and 3dL, respectively). All other substitutions had moderately (I3aV) or relatively strong (I3dV, I3aQ and I3dA) destabilizing effects or were even disruptive (I3aA, I3aS, I3dQ and I3dS).

The observation that leucine appears to be a well-tolerated core substitution was somewhat unexpected in view of the general idea that leucines are preferred in so-called dimeric “leucine zippers” [Harbury et al. Science 1993, 262:1401-1407]. However, the crude rules that were derived in the latter study may not be fully applicable to our reference peptide, since the authors analyzed variants of the GCN4 leucine zipper peptide, which are known to depend on inter-chain ionic interactions between charged residues at e- and g-positions, whereas these positions are occupied by neutral glutamines in our examples. Nevertheless, our observation that valine is tolerated better at a- than at d-positions is in line with the findings of Harbury et al. [ibid].

The additional mutants having glutamine, alanine or serine at core positions are all markedly unstable. These findings can be further extrapolated to other possible core substitutions: in view of the chemical equivalence between leucine and methionine, and the presence of a methionine at the C-terminal core position in our reference peptide, it can be expected that this residue type, together with leucine and the “standard” isoleucine, and to a lesser extent, valine, are tolerated at core positions. Other amino acid residue types are shown and expected to be highly destabilizing. Further, in view of the fact that non-isoleucine core residues increase the propensity of the peptides to form oligomers other than trimers [Harbury et al. Science 1993, 262:1401-1407], isoleucine is a highly preferred core residue. Leucine, methionine and, to a lesser extent, valine, are less preferred core residues. All other residue types are non-preferred core residues.

Example 6

Analysis of Non-Core Mutants

To determine whether or not trimeric coiled coil scaffolds are tolerant to substitutions of non-core residues, various single and double mutants were made of the reference peptide of Example 3 (SEQ ID NO: 6). CD thermal scans were recorded and analyzed in the same way as in Examples 3-5.

The amino acid proline is known to be structurally disruptive in alpha-helices. Glycine has a very low alpha-helical propensity but is generally not disruptive. All other residue types are compatible with alpha-helices but each have a different helical propensity. Moreover, it has been demonstrated that particular non-core residues, especially at e- and g-positions can significantly influence the stability of a coiled coil, at least in dimers but likely also in trimeric complexes [Yu Adv Drug Deliv Rev 2002, 54:1113-1129]. For the purpose of this example, we selected and introduced a representative number of residue types at non-core positions and tested their effect on the stability of the trimeric scaffold structure formed by the reference peptide of Example 3, denoted as “Q2a” (SEQ ID NO: 6). It would be useful to test these mutations within the context of the thermally stable Q2aI mutant of Example 4 (having an all-isoleucine core) (SEQ ID NO: 7) in order to demonstrate tolerance of this preferred scaffold to a variety of amino acid substitutions, such tolerance being a required property of a useful scaffold.

However, the latter experiments would likely prevent quantitative determination of stability effects (see Example 4). Therefore, the moderately stable reference peptide Q2a (with glutamine at core position 2a) was selected as a practically more suitable context. In view of the fact that core and non-core residues are spatially separated in a coiled coil structure (see Example 2), there is little or no doubt that at least the general experimental observations apply to coiled coils with different core substitutions. For the purpose of this example, leucine (L), tryptophan (W), glutamic acid (E) and arginine (R) were selected as representative aliphatic, aromatic, negatively charged and positively charged amino acids, respectively; the latter amino acids should preferably be tolerated by the scaffold.

In addition, the "control" amino acid proline was selected, which should be disruptive if the scaffold structure folds in the way as intended. The said amino acid residue types were substituted at the non-core positions b and c of the third heptad (i.e., at positions 3b and 3c) in peptide Q2a. The list of selected amino acids was further amended for testing mutability at e- and g-positions in the second heptad (i.e., at positions 2e and 2g) in peptide Q2a. At these positions, the amino acids glycine (G), serine (S), tyrosine (Y), asparagine (N) and aspartic acid (D) were also tested. In addition, certain combination mutants of tryptophan, aspartic acid, glutamic acid and arginine at e- and g-positions in the second heptad of peptide Q2a were also tested in order to examine additivity of point mutations.

Figure 10:
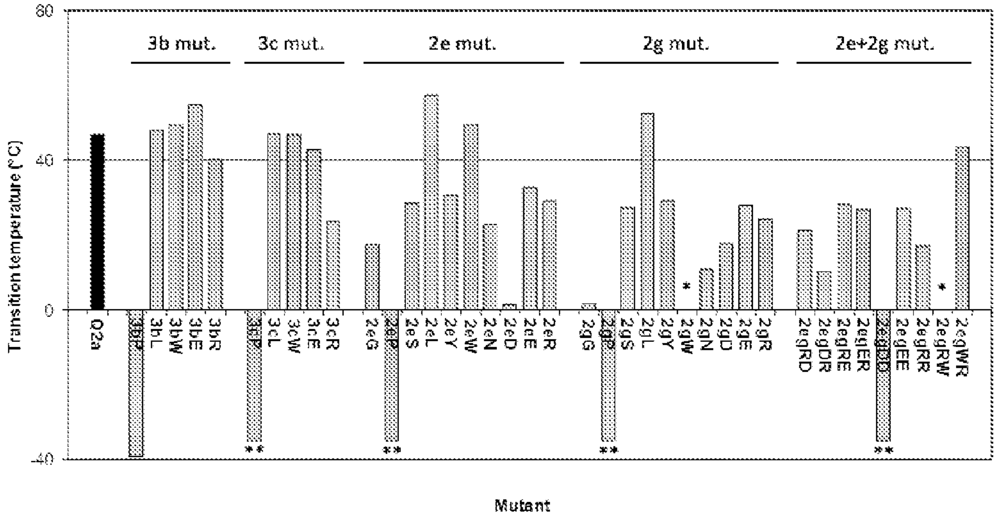

FIG. 10 shows the experimentally determined transition temperatures (bars) for the tested point and double mutants. The mutants are denoted by the position of the mutation followed by the mutant residue type in single-letter notation (for example, "3bL" indicates leucine at position 3b). Double mutants are denoted by the modified heptad, followed by the modified positions, followed by the mutant single-letter residue types at the respective positions (for example, "2egRD" indicates arginine at 2e and aspartic acid at 2g). Mutants labeled by a single asterisk (*) were not determined because they could not be synthesized to sufficient purity. Mutants labeled by a double asterisk (**) were highly unstable, having transition temperatures presumably below −35° C., and the corresponding values were fixed at this value. Compared to the reference sequence of Q2a (carrying alanine at positions 3b and 3c and glutamine at 2e and 2g), it is firstly seen that there are more destabilizing than stabilizing mutations, suggesting that the chosen reference sequence is one of the more preferred (with Q2aI being an even more preferred sequence, see Example 4).

It is also found that the majority of mutations are only moderately stabilizing or destabilizing (with transition temperatures in the range 20-60° C.). In this regard, one needs to take into account that a single substitution in a peptide sequence corresponds to a triple mutation in the trimeric coiled coil structure.

It appears that e,g-mutations have a somewhat higher impact on thermal stability than b,c-substitutions. This may be partly due to the fact that e,g-positions are more buried than b,c-positions (causing a greater desolvation penalty, especially for small, polar amino acids such as serine, asparagine and aspartic acid) and partly due to the breaking of glutamine-glutamine interactions in the Q2a reference structure.

All proline mutations are disruptive, as expected for this amino acid type in alpha-helices.

The double mutations have a largely, though not completely, additive effect. For example, the two double mutants comprising the strongly destabilizing 2eD substitution (2egDR and 2egDD) are also the two least stable double mutants, but 2egDR has a higher transition temperature than 2eD despite the moderately unfavorable effect of 2gR. Possibly, pairwise electrostatic (charge-charge, ionic, Coulombic) interactions play some additional role in the double e,g-mutants, as can also be inferred from the other double mutants 2egRD, 2egRE, 2egER.

However, such pairwise ionic interactions between e- and g-positions are found to be very small, if not negligible, within the context of the trimeric coiled coil scaffold. The latter is also supported by the double mutants 2egEE and 2egRR (having pairs of negative and positive charges, respectively) which do not show specific destabilizing effects that could be expected on grounds of charge-charge repulsion between e- and g-positions. In any case, none of the double mutants having side chains of opposite charge at e- and g-positions was found to require, or benefit from, ionic e,g-interactions; on the contrary, all such mutants were found to be (somewhat) less stable than the reference scaffold having glutamine at each e- and g-position.

Based on these results, it can be concluded that for trimeric coiled coils, in contrast to dimeric coiled coils (Yu Adv Drug Deliv Rev 2002, 54:1113-1129), there is no experimental evidence that ionic e,g-interactions are required or desirable for the stability of the scaffold. Consequently, preferred embodiments of the present invention relate to scaffolds lacking such interactions. More specifically, preferred embodiments of the present invention relate to trimeric scaffolds comprising heptad repeats which have glutamine at e- and g-positions, as is the case in the tested Q2a and Q2I reference scaffolds.

A representative number of amino acid substitutions at characteristic non-core positions were tested in a trimeric coiled coil scaffold: 1 amino acid (lysine) at the very exposed f-position, 5 at the largely exposed b- and c-positions, and 10 at the moderately exposed e- and g-positions. As a rule, the more buried an amino acid is in a certain tertiary structure, the more interactions it makes with the remainder of the structure, and the more critical its nature (and changes therein) will be with respect to the stability of the tertiary structure. Reversely, the more exposed (solvent-oriented) an amino acid, the less critical will be its identity in the sense that mutations at this position will be better tolerated by (have a lower impact on) the tertiary structure.

Since, for practical reasons, not all possible substitutions can be tested, the number of selected mutants was chosen in accordance with aforementioned rules regarding the correlation between degree of exposure and mutability. Furthermore, since even at the least exposed non-core (e,g-) positions the majority of amino acid types are tolerated (have a low or moderate impact on stability), it will be clear for persons skilled in the field of protein engineering that a very large number of multiple substitutions and, hence, specific amino acid sequences other than the ones tested, will also yield stable trimeric, parallel, alpha-helical coiled coil structures. Therefore, preferred embodiments of the present invention relate to scaffold molecules formed by reference peptides Q2a and Q2aI, wherein one or more of the non-core amino acids are substituted into another amino acid type than present in the reference peptides.

One particular scaffold variant, namely the trimeric coiled coil having all-alanine at the non-core positions b, c, e, f and g, forms a special case, in that, it represents the essence of what is generally understood by a scaffold molecule, i.e., a molecule that acts as a carrier of chemical groups. All natural amino acids (except proline) have the same backbone (main chain) atoms, but differ in the composition of their side chains. Apart from glycine, all natural amino acids have at least one carbon atom (beta carbon, C-beta, CB) to which the remainder of the side-chain atoms are attached. Alanine only has a (hydrogen-saturated) beta carbon atom. Other amino acids (except glycine) are thus formally alanines wherein particular chemical groups are attached to the beta carbon atom.

Thus, alanine represents the 'chemically pure' instance of a carrier amino acid, and proteins displaying alanines at their surface form 'chemically pure' instances of scaffold molecules onto which other side-chain types can be attached.

Accordingly, a most preferred (because chemically pure) embodiment of the present invention relates to a trimeric coiled coil scaffold wherein all non-core amino acids are alanines. Because of the intrinsically high mutability of non-core amino acids, as demonstrated in the present example, other preferred embodiments of the present invention relate to variants of the latter scaffold wherein one or more of the non-core amino acids are substituted into another amino acid type than alanine.

Example 7

Attachment of Tags at the Scaffold's Termini

To determine whether the trimeric scaffolds can be supplemented (combined) with chemical moieties (tags) that are useful for purification and/or detection, biotin and c-myc tags were attached to the N- and C-termini, respectively, of both the reference peptide of Example 3, here named Q2a (SEQ ID NO: 6), and the mutant peptide of Example 4, Q2aI (SEQ ID NO: 7). A small serine-glycine spacer fragment was placed in between the tags and the peptides on either side. Thus, tagged Q2a had the sequence biotin-SGMSIEEIQKQQAAIQK-QIAAIQKQIYRMTPSGEQKLISEEDL-NH2 (SEQ ID NO: 8) and tagged Q2aI had the sequence biotin-SGMSIEEIQK-QIAAIQKQIAAIQKQIYRMTPSGEQKLISEEDL-NH2 (SEQ ID NO: 9).

The two peptides were immobilized through the biotin moiety on a neutravidin-coated plate, and the availability of the c-myc tag was tested using a mouse anti-c-myc primary antibody and an anti-mouse horseradish peroxidase (HRP) conjugate as secondary detection system. The untagged peptides were also tested as negative controls. As an additional negative control, the same experiments were performed using non-coated plates. Skimmed milk was used as blocking agent.

Figure 11:
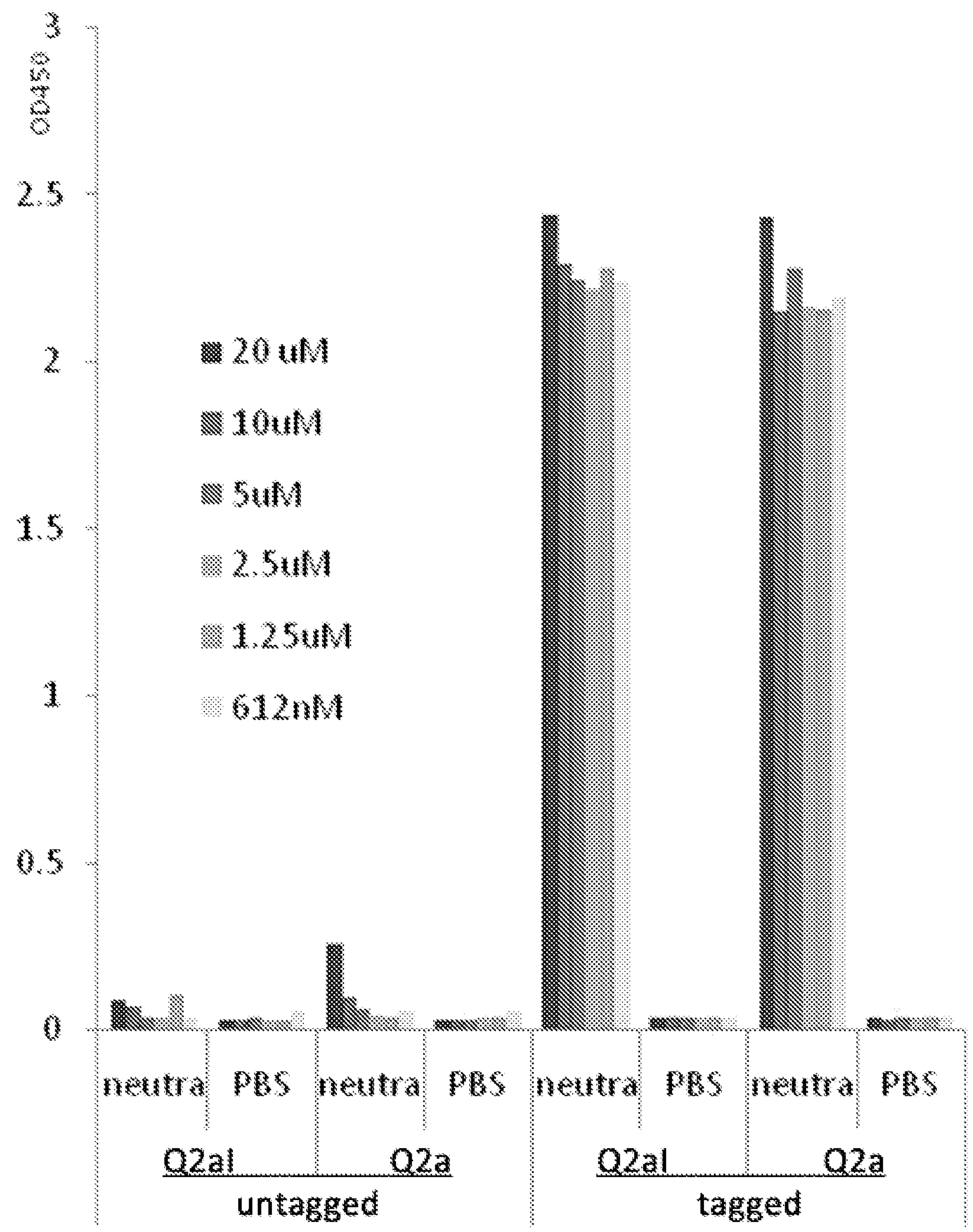

The results of these experiments are shown in FIG. 11. The signal is measured as optical density at 450 nm (OD450). The peptide concentrations were varied by serial dilutions of a factor 2 in the range 20 microM to 612 nanoM, and are listed at the left-hand side of the figure. “neutra” refers to neutravidin-coated plates, whereas “PBS” refers to non-coated plates (buffer only).

FIG. 11 shows positive detection of the tagged peptides, no detection of untagged peptides, and no detection of peptides on non-coated plates. Said positive detection was found to be independent of the concentration of tagged peptides.

Since a strong signal indicates that the anti-c-myc antibody was able to bind to the peptide via the c-myc tag and that the peptide was able to bind to neutravidin on plate via the biotin tag, it was concluded that the tags at both termini are available for binding. In view of the very high stability of the Q2aI variant, it can be reasonably expected that at least this peptide assumes the structure of a trimeric coiled coil. Thus, the results strongly suggest that the trimeric scaffolds of the present invention can be supplemented (combined) with tags that are useful for purification and/or detection of the scaffold.

The invention claimed is:

1. A non-natural, thermodynamically stable, proteinaceous scaffold consisting of three non-covalently associated peptides, wherein each peptide comprises less than 50 amino acid residues and wherein each peptide sequence comprises between 2 and 7 consecutive heptad repeats of the formula cxxcxxx (SEQ ID NO: 10), wherein the characters "c" and "x" denote respectively "core" and "non-core" amino acid residues, and wherein:

(i) a) all, or all except one of the c-residues are isoleucine amino acid residues, the remaining c-residue being a natural or non-natural amino acid residue other than isoleucine and proline;

b) each x-residue is an alanine amino acid residue;

c) the said peptide sequences associate into trimers by way of their heptad repeats forming triple-stranded, parallel, alpha-helical coiled coils wherein the said c-residues form the core; and d) the coiled coil-forming peptide sequences remain associated under physical conditions that are different from physiological conditions being a pH of 7, a temperature of 37° C. and an ionic strength of 0.15 molar; or ii) the peptide sequences having the above features (a), (c) and (d) comprise heptad repeats selected from the group consisting of SEQ ID NO: 1, SEQ ID NO: 2, SEQ ID NO: 3 and SEQ ID NO: 4.

2. The scaffold according to claim 1, wherein one of the c-residues is an amino acid selected from the group consisting of valine, leucine, methionine, phenylalanine, tyrosine, tryptophan, histidine, glutamine, threonine, serine, alanine, glycine, and a derivative thereof.

3. The scaffold according to claim 1, wherein one of the c-residues is an amino acid selected from the group consisting of valine, leucine, methionine, and a derivative thereof.

4. The scaffold according to claim 1, wherein all c-residues are isoleucines.

5. The scaffold according to claim 1, wherein the physical conditions differ by at least two pH units, 20° C., and/or a factor two in ionic strength from the physiological conditions being a pH of 7, a temperature of 37° C., and an ionic strength of 0.15 molar.

6. The scaffold according to claim 1, which binds to a non-immunoglobulin target compound, said binding being characterized by a dissociation constant Kd lower than 1000 micromolar.

7. The scaffold according to claim 1, wherein the physical conditions differ by at least four pH units, 40° C., and/or a factor four in ionic strength from the physiological conditions being a pH of 7, a temperature of 37° C., and an ionic strength of 0.15 molar.

8. The scaffold according to claim 1, which binds to a non-immunoglobulin target compound, said binding being characterized by a dissociation constant Kd lower than 100 micromolar.

9. The scaffold according to claim 1, which binds to a non-immunoglobulin target compound, said binding being characterized by a dissociation constant Kd lower than 10 micromolar.

10. The scaffold according to claim 1, which binds to a non-immunoglobulin target compound, said binding being characterized by a dissociation constant Kd lower than 1 micromolar.

11. The scaffold according to claim 1, wherein one of the c-residues is an amino acid selected from the group consisting of valine, leucine, methionine, phenylalanine, tyrosine, tryptophan, histidine, glutamine, threonine, serine, alanine, and glycine.

12. The scaffold according to claim 1, wherein one of the c-residues is an amino acid selected from the group consisting of valine, leucine, and methionine.

13. A non-natural, thermodynamically stable, proteinaceous scaffold consisting of three non-covalently associated peptides, wherein each peptide comprises less than 50 amino acid residues and wherein each peptide sequence comprises between 2 and 7 consecutive heptad repeats of the formula cxxcxxx (SEQ ID NO: 10), wherein the characters "c" and "x" denote respectively "core" and "non-core" amino acid residues, and wherein:

(i) a) all, or all except one of the c-residues are isoleucine amino acid residues, the remaining c-residue being a natural or non-natural amino acid residue other than isoleucine and proline, wherein one of the c-residues is an amino acid selected from the group consisting of valine, leucine, methionine, phenylalanine, tyrosine, tryptophan, histidine, glutamine, threonine, serine, alanine, glycine, and a derivative thereof;

b) each x-residue is an alanine amino acid residue;

c) the said peptide sequences associate into trimers by way of their heptad repeats forming triple-stranded, parallel, alpha-helical coiled coils wherein the said c-residues form the core; and d) the coiled coil-forming peptide sequences remain associated under physical conditions that are different from physiological conditions being a pH of 7, a temperature of 37° C. and an ionic strength of 0.15 molar; or ii) the peptide sequences having the above features (a), (c) and (d) comprise heptad repeats selected from the group consisting of SEQ ID NO: 1, SEQ ID NO: 2, SEQ ID NO: 3 and SEQ ID NO: 4.

14. A non-natural, thermodynamically stable, proteinaceous scaffold consisting of three non-covalently associated peptides, wherein each peptide comprises less than 50 amino acid residues and wherein each peptide sequence comprises between 2 and 7 consecutive heptad repeats of the formula cxxcxxx (SEQ ID NO: 10), wherein the characters "c" and "x" denote respectively "core" and "non-core" amino acid residues, and wherein:

(i) a) all, or all except one of the c-residues are isoleucine amino acid residues, the remaining c-residue being a natural or non-natural amino acid residue other than isoleucine and proline, wherein one of the c-residues is an amino acid selected from the group consisting of valine, leucine, methionine, and a derivative thereof;

b) each x-residue is an alanine amino acid residue;

c) the said peptide sequences associate into trimers by way of their heptad repeats forming triple-stranded, parallel, alpha-helical coiled coils wherein the said c-residues form the core; and d) the coiled coil-forming peptide sequences remain associated under physical conditions that are different from physiological conditions being a pH of 7, a temperature of 37° C. and an ionic strength of 0.15 molar; or ii) the peptide sequences having the above features (a), (c) and (d) comprise heptad repeats selected from the group consisting of SEQ ID NO: 1, SEQ ID NO: 2, SEQ ID NO: 3 and SEQ ID NO: 4.

* * * * *

SEQUENCE LISTING

```
<160> NUMBER OF SEQ ID NOS: 14

<210> SEQ ID NO 1
<211> LENGTH: 14
<212> TYPE: PRT
<213> ORGANISM: Artificial Sequence
<220> FEATURE:
<223> OTHER INFORMATION: Synthetic Construct

<400> SEQUENCE: 1

Ile Ala Ala Ile Ala Ala Ala Ile Ala Ala Ile Ala Ala Ala
1               5                   10


<210> SEQ ID NO 2
<211> LENGTH: 14
<212> TYPE: PRT
<213> ORGANISM: Artificial Sequence
<220> FEATURE:
<223> OTHER INFORMATION: Synthetic Construct

<400> SEQUENCE: 2

Ile Ala Ala Ile Gln Lys Gln Ile Ala Ala Ile Gln Lys Gln
1               5                   10


<210> SEQ ID NO 3
<211> LENGTH: 21
<212> TYPE: PRT
<213> ORGANISM: Artificial Sequence
<220> FEATURE:
<223> OTHER INFORMATION: Synthetic Construct

<400> SEQUENCE: 3

Ile Ala Ala Ile Ala Ala Ala Ile Ala Ala Ile Ala Ala Ala Ile Ala
1               5                   10                  15

Ala Ile Ala Ala Ala
```

20

<210> SEQ ID NO 4
<211> LENGTH: 21
<212> TYPE: PRT
<213> ORGANISM: Artificial Sequence
<220> FEATURE:
<223> OTHER INFORMATION: Synthetic Construct

<400> SEQUENCE: 4

```
Ile Ala Ala Ile Gln Lys Gln Ile Ala Ala Ile Gln Lys Gln Ile Ala
1               5                   10                  15

Ala Ile Gln Lys Gln
            20
```

<210> SEQ ID NO 5
<211> LENGTH: 24
<212> TYPE: PRT
<213> ORGANISM: Artificial Sequence
<220> FEATURE:
<223> OTHER INFORMATION: Synthetic Construct

<400> SEQUENCE: 5

```
Ala Ile Ala Ala Ile Gln Lys Gln Ile Ala Ala Leu Gln Lys Gln Ile
1               5                   10                  15

Ala Ala Ile Gln Lys Gln Ile Ala
            20
```

<210> SEQ ID NO 6
<211> LENGTH: 29
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (29)..(29)
<223> OTHER INFORMATION: AMIDATION

<400> SEQUENCE: 6

```
Met Ser Ile Glu Glu Ile Gln Lys Gln Gln Ala Ala Ile Gln Lys Gln
1               5                   10                  15

Ile Ala Ala Ile Gln Lys Gln Ile Tyr Arg Met Thr Pro
            20                  25
```

<210> SEQ ID NO 7
<211> LENGTH: 29
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (29)..(29)
<223> OTHER INFORMATION: AMIDATION

<400> SEQUENCE: 7

```
Met Ser Ile Glu Glu Ile Gln Lys Gln Ile Ala Ala Ile Gln Lys Gln
1               5                   10                  15
```

-continued

```
Ile Ala Ala Ile Gln Lys Gln Ile Tyr Arg Met Thr Pro
            20                  25
```

<210> SEQ ID NO 8
<211> LENGTH: 43
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Biotinylation
<220> FEATURE:
<221> NAME/KEY: MOD_RES
<222> LOCATION: (43)..(43)
<223> OTHER INFORMATION: AMIDATION

<400> SEQUENCE: 8

```
Ser Gly Met Ser Ile Glu Glu Ile Gln Lys Gln Gln Ala Ala Ile Gln
1               5                   10                  15

Lys Gln Ile Ala Ala Ile Gln Lys Gln Ile Tyr Arg Met Thr Pro Ser
            20                  25                  30

Gly Glu Gln Lys Leu Ile Ser Glu Glu Asp Leu
        35                  40
```

<210> SEQ ID NO 9
<211> LENGTH: 43
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Biotinylation
<220> FEATURE:
<221> NAME/KEY: MOD_RES
<222> LOCATION: (43)..(43)
<223> OTHER INFORMATION: AMIDATION

<400> SEQUENCE: 9

```
Ser Gly Met Ser Ile Glu Glu Ile Gln Lys Gln Ile Ala Ala Ile Gln
1               5                   10                  15

Lys Gln Ile Ala Ala Ile Gln Lys Gln Ile Tyr Arg Met Thr Pro Ser
            20                  25                  30

Gly Glu Gln Lys Leu Ile Ser Glu Glu Asp Leu
        35                  40
```

<210> SEQ ID NO 10
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa is any natural or non-natural amino acid other than Proline
<220> FEATURE:
<221> NAME/KEY: MISC_FEATURE
<222> LOCATION: (2)..(3)
<223> OTHER INFORMATION: Xaa is any natural or non-natural amino acid
<220> FEATURE:
<221> NAME/KEY: MISC_FEATURE
<222> LOCATION: (4)..(4)
<223> OTHER INFORMATION: Xaa is any natural or non-natural amino acid other than Proline
<220> FEATURE:

<221> NAME/KEY: MISC_FEATURE
<222> LOCATION: (5)..(7)
<223> OTHER INFORMATION: Xaa is any natural or non-natural amino acid

<400> SEQUENCE: 10

Xaa Xaa Xaa Xaa Xaa Xaa Xaa
1               5

<210> SEQ ID NO 11
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa is a hydrophobic residue
<220> FEATURE:
<221> NAME/KEY: MISC_FEATURE
<222> LOCATION: (2)..(3)
<223> OTHER INFORMATION: Xaa is a polar residue
<220> FEATURE:
<221> NAME/KEY: MISC_FEATURE
<222> LOCATION: (4)..(4)
<223> OTHER INFORMATION: Xaa is a hydrophobic residue
<220> FEATURE:
<221> NAME/KEY: MISC_FEATURE
<222> LOCATION: (5)..(7)
<223> OTHER INFORMATION: Xaa is a polar residue

<400> SEQUENCE: 11

Xaa Xaa Xaa Xaa Xaa Xaa Xaa
1               5

<210> SEQ ID NO 12
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(3)
<223> OTHER INFORMATION: Xaa is any natural or non-natural amino acid
<220> FEATURE:
<221> NAME/KEY: MISC_FEATURE
<222> LOCATION: (5)..(7)
<223> OTHER INFORMATION: Xaa is any natural or non-natural amino acid

<400> SEQUENCE: 12

Ile Xaa Xaa Leu Xaa Xaa Xaa Val
1               5

<210> SEQ ID NO 13
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa is Leucine, Isoleucine, or Valine
<220> FEATURE:
<221> NAME/KEY: MISC_FEATURE
<222> LOCATION: (2)..(3)
<223> OTHER INFORMATION: Xaa is any natural or non-natural amino acid
<220> FEATURE:
<221> NAME/KEY: MISC_FEATURE
<222> LOCATION: (4)..(4)
<223> OTHER INFORMATION: Xaa is Leucine, Isoleucine, or Valine
<220> FEATURE:

-continued

```
<221> NAME/KEY: MISC_FEATURE
<222> LOCATION: (5)..(7)
<223> OTHER INFORMATION: Xaa is any natural or non-natural amino acid
<220> FEATURE:
<221> NAME/KEY: MISC_FEATURE
<222> LOCATION: (8)..(8)
<223> OTHER INFORMATION: Xaa is Leucine, Isoleucine, or Valine

<400> SEQUENCE: 13

Xaa Xaa Xaa Xaa Xaa Xaa Xaa Xaa
1               5


<210> SEQ ID NO 14
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (6)..(6)
<223> OTHER INFORMATION: AMIDATION

<400> SEQUENCE: 14

Ile Tyr Arg Met Thr Pro
1               5
```